United States Patent
DiCosimo et al.

(10) Patent No.: US 7,612,030 B2
(45) Date of Patent: Nov. 3, 2009

(54) ENZYMATIC PRODUCTION OF PERACIDS USING PERHYDROLYTIC ENZYMES

(75) Inventors: Robert DiCosimo, Chadds Ford, PA (US); Mark S. Payne, Wilmington, DE (US); Vincent Brian Croud, Sheffield (GB); John E. Gavagan, Wilmington, DE (US); Lorraine W. Wagner, Newark, DE (US); Eugenia Costa Hann, Carneys Point, NJ (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 215 days.

(21) Appl. No.: 11/413,246

(22) Filed: Apr. 28, 2006

(65) Prior Publication Data

US 2007/0105740 A1   May 10, 2007

Related U.S. Application Data

(60) Provisional application No. 60/676,116, filed on Apr. 29, 2005.

(51) Int. Cl.
*C11D 3/39* (2006.01)
*C11D 3/395* (2006.01)
*C11D 3/386* (2006.01)
*A01N 25/00* (2006.01)

(52) U.S. Cl. ............ 510/303; 422/28; 422/29; 424/94.2; 424/405; 435/129; 435/134; 435/135; 435/136; 435/264; 510/226; 510/300; 510/305; 510/306; 510/310; 510/375; 510/393

(58) Field of Classification Search ............ None
See application file for complete search history.

(56) References Cited

U.S. PATENT DOCUMENTS

| | | | |
|---|---|---|---|
| 3,974,082 A | 8/1976 | Weyn | |
| 4,585,150 A | 4/1986 | Beacham et al. | |
| 5,116,575 A | 5/1992 | Badertscher et al. | |
| 5,296,161 A | 3/1994 | Wiersema et al. | |
| 5,352,594 A * | 10/1994 | Poulouse | 435/6 |
| 5,364,554 A | 11/1994 | Stanisloski et al. | |
| 5,398,846 A | 3/1995 | Corba et al. | |
| 5,431,843 A * | 7/1995 | Mitchell et al. | 252/186.38 |
| 5,458,802 A * | 10/1995 | Sanderson et al. | 510/371 |
| 5,486,212 A * | 1/1996 | Mitchell et al. | 8/142 |
| 5,561,235 A * | 10/1996 | Gosselink et al. | 546/210 |
| 5,584,888 A * | 12/1996 | Miracle et al. | 8/111 |
| 5,624,634 A | 4/1997 | Brougham et al. | |
| 5,683,724 A | 11/1997 | Hei et al. | |
| 5,932,532 A | 8/1999 | Ghosh et al. | |
| 6,183,807 B1 | 2/2001 | Gutmann et al. | |
| 6,210,639 B1 | 4/2001 | Vlass et al. | |
| 6,319,888 B2 | 11/2001 | Wei et al. | |
| 6,391,840 B1 | 5/2002 | Thompson et al. | |
| 6,432,661 B1 * | 8/2002 | Heitfeld et al. | 435/27 |
| 6,509,308 B1 * | 1/2003 | De Buzzaccarini et al. | 510/372 |
| 6,518,307 B2 | 2/2003 | McKenzie et al. | |
| 6,545,047 B2 | 4/2003 | Gutzmann et al. | |
| 6,763,888 B1 | 7/2004 | Harris et al. | |
| 6,995,125 B2 | 2/2006 | Dasque et al. | |
| 2002/0172989 A1 | 11/2002 | Shih | |
| 2003/0026846 A1 | 2/2003 | Hei et al. | |
| 2005/0008526 A1 | 1/2005 | Bianchetti et al. | |
| 2005/0139608 A1 | 6/2005 | Muehlhausen et al. | |

FOREIGN PATENT DOCUMENTS

| | | |
|---|---|---|
| EP | 0 807 156 B1 | 11/1997 |
| WO | WO 00/11713 A1 | 3/2000 |
| WO | WO 2004/039418 A1 | 5/2004 |

OTHER PUBLICATIONS

M.R. Gray, Substrate Inactivation of Enzymes in Vitro and in Vivo, Biotech. ADV., 1989, vol. 7:527-575.
K. Kleppe, the Effect of Hydrogen Peroxide on Glucose Oxidase From *Aspergillus niger*, Biochemistry, 1966, vol. 5:139-143.
D.A. Estell et al., Engineering an Enzyme by Site Directed Mutagenesis to be Resistant to Chemical Oxidation, J. Biol. Chem., 1985, vol. 260:6518-6521.
M.B. Arnao et al., A Kinetic Study on the Suicide Inactivation of Peroxidase by Hydrogen Peroxide, Biochim. Biophys. Acta, 1990, vol. 1041-43.
B. Valderrama et al., Suicide Inactivation of Peroxidases and the Challenge of Engineering More Robust Enzymes Chemistry& Biology 2002 vol. 9:555-565.
P.F. Greenfield et al., Inactivation of Immobilized Glucose Oxidase by Hydrogen Peroxide.Anal. Biochem., 1975, vol. 65:109-124.
F. Lopez-Gallego et al., One-Pot Conversion of Cephalosporin C to 7=Aminocephalosporanic Acid in the Absence of Hydrogen Peroxide, Adv. Synth. Catal., 2005, vol. 347:1804.
O. Kirk et al., Enzyme Catalyzed Degradation and Formation of Peroxycarboxylic Acids, Biocatalysis, 1994, vol. 11:65-77.
Langeveld et al., Enzymatic Degradation of Prion Protein in Brain Stem From Infected Cattle and Sheep, J. Infect. Diseases, 2003, vol. 188:1782-1789.
U. Karst et al., Simultaneous HPLC Determination of Peroxyacetic Acid and Hydrogen Peroxide, Anal. Chem., 1997, vol. 69:3623-3627.
J. Gabrielson et al., Evaluation of Redox Indicators and the Use of Digital Scanners and Spectrophotometer for Quantification of Microbial Growth in Microplates, J.of Micro. Methods, 2000, vol. 50:63-73.
Georgios T. Papageorgiou et al., New Method for Evaluation of Virucidal Activity of Antiseptics and Disinfectants, Appl. Environ. Microbiol., 2001, vol. 67:5844-5848.

* cited by examiner

*Primary Examiner*—Herbert J. Lilling

(57) ABSTRACT

A process is provided to produce a concentrated aqueous peracid solution in situ using at least one enzyme having perhydrolase activity in the presence of hydrogen peroxide (at a concentration of at least 500 mM) under neutral to acidic reaction conditions from suitable carboxylic acid esters (including glycerides) and/or amides substrates. The concentrated peracid solution produced is sufficient for use in a variety of disinfection and/or bleaching applications.

32 Claims, No Drawings

ENZYMATIC PRODUCTION OF PERACIDS USING PERHYDROLYTIC ENZYMES

This application claims the benefit of U.S. Provisional Application No. 60/676,116 filed Apr. 29, 2005.

FIELD OF THE INVENTION

This invention relates to the field of organic peracid synthesis and enzyme catalysis.

BACKGROUND OF THE INVENTION

Peracids have been used for disinfection in a number of applications. U.S. Pat. No. 6,545,047 B1 describes a method for sanitizing animal carcasses using antimicrobial compositions containing one or more peracids. U.S. Pat. No. 6,183,807 B1 describes a method for cleaning and sanitizing meat products using antimicrobial compositions containing one or more peracids. U.S. Pat. No. 6,518,307 B2 describes a method for controlling microbial populations in the gastrointestinal tract of animals by orally administering an effective amount of peracid. U.S. Patent Appln. Pub. No. 20030026846 A1 describes a method of using peracid/acid compositions to control pathogenic organisms on living plant tissue. U.S. Pat. No. 5,683,724 describes a process for preventing microbial growth in aqueous streams used for transporting or processing food products and packaged foods that uses an effective antimicrobial concentration of peracid.

Peracids can be prepared by the chemical reaction of a carboxylic acid and hydrogen peroxide (see *Organic Peroxides*, Daniel Swern, ed., Vol. 1, pp 313-516; Wiley Interscience, N.Y.). The reaction is usually catalyzed by a strong inorganic acid, such as concentrated sulfuric acid. The reaction of hydrogen peroxide with a carboxylic acid is an equilibrium reaction, and the production of peracid is favored by the use of an excess concentration of peroxide and/or carboxylic acid, or by the removal of water. There are several disadvantages to the chemical reaction for peracid production: a) the high concentration of carboxylic acid used to favor production of peracid can result in an undesirable odor when using the peracid-containing solution, 2) the peracid is oftentimes unstable in solution over time, and the concentration of peracid in the solution decreases during storage prior to use, and 3) the formulation is often strongly acidic due to the use of a concentrated sulfuric acid as catalyst. One way to overcome the disadvantages of the chemical production of peracids is to employ an enzyme catalyst in place of a strong acid catalyst. The use of an enzyme catalyst allows for the rapid production of peracid at the time of use, avoiding the problem of storage of peracid solutions and of using chemically-produced peracid solutions containing an unknown concentration of peracid. The high concentrations of carboxylic acids typically used to produce peracid via the direct chemical reaction with hydrogen peroxide are not required for enzymatic production of peracid, where the enzyme-catalyzed reaction can use a carboxylic acid ester or amide as substrate at a much lower concentration than is typically used in the chemical reaction. The enzyme reaction can be performed across a broad range of pH, dependent on enzyme activity and stability at a given pH, and on the substrate specificity of the enzyme for perhydrolysis at a given pH.

Enzymes can catalyze the perhydrolysis of esters and amides to produce the corresponding peroxycarboxylic acids (Equations 1 and 2), however, most known methods for preparing peracids from the corresponding carboxylic acid esters or amides using enzyme catalysts do not produce and accumulate a peracid at a sufficiently-high concentration to be efficacious for disinfection in a variety of applications.

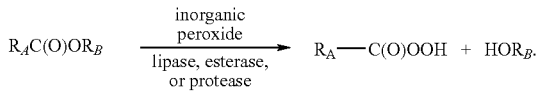

Equation 1

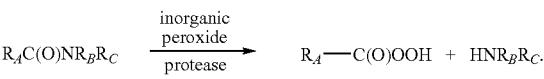

Equation 2

The use of hydrogen peroxide as an enzyme substrate for the enzymatic perhydrolysis of carboxylic acid esters or amides can be problematic, as hydrogen peroxide is known to oxidatively inactivate numerous enzymes (M. R. Gray, *Biotech Adv.*, 7:527 (1989)). K. Kleppe (*Biochemistry*, 5:139 (1966)) report that hydrogen peroxide inactivates enzymes by modifying certain amino acid residues in proteins, where at acid pH values methionine is easily oxidized to methionine sulfoxide, and at basic pH values tryptophan is destroyed. D. A. Estell et al. (*J. Biol. Chem.*, 260:6518 (1985)) describe inactivation of enzymes containing methionine, cysteine or tryptophan residues by hydrogen peroxide, and demonstrate >80% inactivation of the protease subtilisin from *Bacillus amyloliquefaciens* in less than 6 minutes or 4 minutes using 0.1 M or 1.0 M hydrogen peroxide, respectively. Inactivation of peroxidases by 5 mM to 50 mM hydrogen peroxide is reported by M. B. Amao et al. (*Biochim. Biophys. Acta*, 1041:43 (1990)), and B. Valderrama et al. (*Chemistry & Biology*, 9:555 (2002)) review the inactivation of peroxidases by oxidative species such as hydrogen peroxide. P. F. Greenfield et al. (*Anal. Biochem.*, 65:109 (1975)) report an increase in inactivation of glucose oxidase with increasing hydrogen peroxide concentration. For the conversion of cephalosporin C to 7-aminocephalosporanic acid, both a D-amino acid oxidase and a glutaryl acylase were inactivated by the byproduct hydrogen peroxide produced by the oxidase (F. Lopez-Gallego, et al., *Adv. Synth. Catal.*, 347:1804 (2005)). In view of these and other teachings, previously reported methods for enzymatic production of peracid utilize low concentrations of added hydrogen peroxide, where a low concentration of hydrogen peroxide would be expected to reduce or limit enzyme inactivation during the perhydrolysis reaction.

U.S. Pat. No. 3,974,082 ("the '082 patent") describes the production of bleaching compositions for laundry detergent applications by contacting the material to be bleached with an aqueous solution containing an oxygen-releasing inorganic peroxygen compound, an acyl alkyl ester, and an esterase or lipase capable of hydrolyzing the ester. The bleaching compositions cited in the '082 patent are highly alkaline (using such buffering agents as pentasodium tripolyphosphate or sodium carbonate), and no data is presented for either the concentration of peracids produced in the cited compositions, or for the utility of the cited compositions for bleaching of laundry. The bleaching compositions cited in the '082 patent contain up to 40% by weight of per-compound, for example, hydrogen peroxide or alkali metal salts of percarbonate, perborate, persilicate and perphosphate. The bleaching compositions are added to water in amounts up to 12.5 grams per liter of water to initiate the enzyme-catalyzed perhydrolysis reaction, where the maximum concentration of hydrogen peroxide present in the enzyme-catalyzed perhydrolysis reaction is 5 grams/liter, equivalent to ca. 147 mM hydrogen peroxide.

U.S. Pat. No. 5,296,161 ("the '161 patent") describes an activated oxidant system providing enhanced stain removing ability in both high and low temperature wash applications. The oxidant system is capable of in situ generation of >0.1 ppm peracid by enzymatic perhydrolysis, where in the absence of added enzyme the ester substrate is incapable of substantial chemical perhydrolysis. The oxidant system uses a source of peroxygen, a lipase or esterase, and glycerides or monoacylated ethylene glycol or propylene glycol derivatives to generate peracid. The most-preferred enzyme substrate in the '161 patent oxidant system is either trioctanoin or tridecanoin, the enzymatic reaction is carried out at a pH of from 7.5 to 11.0, and none of the accompanying examples demonstrate the production of greater than 10 ppm of peracid. The highest concentration of hydrogen peroxide present in the exemplified perhydrolysis reactions was 1314 ppm, equivalent to ca. 38.6 mM $H_2O_2$.

U.S. Pat. No. 5,364,554 describes an activated oxidant system for in situ generation of peracid in aqueous solution using a protease enzyme, a source of hydrogen peroxide, and an ester substrate that is preferably chemically non-perhydrolyzable. A method of bleaching and a method of forming peracid are also disclosed. The enzymatic reactions are carried out at a pH of from about 8.0 to 10.5, and none of the accompanying examples demonstrate the production of greater than 5 ppm of peracid. The concentration of hydrogen peroxide present in the exemplified perhydrolysis reactions was 400 ppm, equivalent to ca. 11.8 mM $H_2O_2$.

O. Kirk et al. (*Biocatalysis*, 11:65-77 (1994)) investigated the ability of hydrolases (lipases, esterases, and proteases) to catalyze perhydrolysis of acyl substrates with hydrogen peroxide to form peroxycarboxylic acids, and reported that perhydrolysis proceeds with a very low efficiency in aqueous systems. Furthermore, they found that lipases and esterases degraded percarboxylic acid to the corresponding carboxylic acid and hydrogen peroxide. They also found that proteases neither degraded nor catalyzed perhydrolysis of carboxylic acid esters in water. The authors concluded that esterases, lipases and proteases are, in general, not suitable for catalyzing perhydrolysis of simple esters, such as methyl octanoate and trioctanoin, in an aqueous environment.

The problem to be solved is to provide an aqueous enzymatic process for in situ production of peracid compositions under neutral to acidic conditions from non-toxic and inexpensive carboxylic acid esters, amides, and/or glycerides at concentrations suitable for use as a disinfectant in a variety of applications. Preferably, the process will produce a concentrated aqueous solution of peracid within at least about 5 minutes. As such, the enzymatic perhydrolysis process should occur in the presence of at least 500 mM hydrogen peroxide (peroxygen source). It has been reported that for certain disinfecting, cleaning or bleaching applications a non-alkaline peracid solution is preferred. As such, the process should produce an aqueous peracid solution in a single step under neutral to acidic conditions, more preferably under acidic conditions. The process preferably needs to produce peracid compositions comprised of at least 10 ppm peracid (for example peracetic acid), more preferably at least 100 ppm, and even more preferably in the range of about 100 to about 5000 ppm, where the resulting peracid composition can be used directly, or diluted to the desired concentration of peracid prior to use, to produce a 5-log or 6-log reduction in the concentration of the targeted infectious microorganism in about 5 minutes to about 10 minutes, at temperatures ranging from about 0° C. to about 60° C., preferably about 4° C. to about 30° C., most preferably about 10° C. to about 25° C.

A second problem to solve is to provide a process to produce a multi-functional composition that has disinfecting, bleaching and prion-degrading activity. The process should produce an aqueous peracid solution in situ comprising a sufficient disinfecting and/or bleaching concentrations of peracid and one or more prion-degrading proteases.

An additional problem to be solved is the lack of a combination of enzyme catalyst and enzyme substrate that results in the conversion of carboxylic acid esters or amides to percarboxylic acid at a concentration more efficacious for bleaching in laundry applications, compared to the concentrations of peracids previously disclosed in the prior art. A solution to the problem needs to 1) efficiently produce an aqueous solution of peracid where the peracid is present in sufficient concentration to act as a disinfectant or bleaching agent, 2) use an enzyme catalyst having suitable perhydrolase activity for converting carboxylic acid esters, amides, and/or glycerides to the corresponding peracids in aqueous solution; 3) provide methods to improve catalyst stability to increase the catalyst productivity, thereby decreasing catalyst cost; and 4) provide methods to efficiently and economically obtain peracids from relatively inexpensive and non-toxic starting materials.

SUMMARY OF THE INVENTION

The stated problems have been solved by providing a process to produce an aqueous peracid solution in situ using at least one enzyme having perhydrolase activity in the presence of hydrogen peroxide (at a concentration of at least 500 mM) under neutral to acidic reaction conditions from suitable carboxylic acid esters (including glycerides) and/or amides substrates. The concentration of peracid produced is sufficient for use in a variety of disinfection and/or bleaching applications.

One aspect of the invention provides a process for producing a concentrated aqueous peracid solution comprising;

a) providing a set of peracid reaction components, said components comprising:

1) at least one substrate selected from the group consisting of:

i) esters having the structure

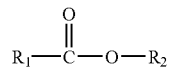

wherein $R_1$=C1 to C10 straight chain or branched chain alkyl optionally substituted with an hydroxyl or a C1 to C4 alkoxy group and $R_2$=C1 to C10 straight chain or branched chain alkyl group, $(CH_2CH_2-O)_nH$ or $(CH_2CH(CH_3)-O)_nH$ and n=1 to 10;

ii) glycerides having the structure

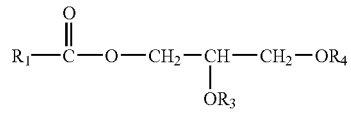

wherein $R_1$=C1 to C10 straight chain or branched chain alkyl optionally substituted with an hydroxyl or a C1 to C4 alkoxy group and $R_3$ and $R_4$ are individually H or $R_1C(O)$; and iii) amides having the structure:

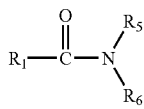

wherein $R_5$ and $R_6$=H or a C1 to C5 straight chain or branched alkyl group;
2) a source of peroxygen that provides a concentration of at least 500 mM hydrogen peroxide upon combining said reaction components; and
3) at least one enzyme catalyst having perhydrolase activity, wherein said enzyme catalyst is selected from the group consisting of lipases, esterases, proteases, and mixtures thereof; and b) combining said reaction components at a pH of about 2.5 to about 7.5, whereby a concentrated peracid solution is produced within at least about 5 minutes to about 2 hours after combining said reaction components.

This process produces a concentrated peracid solution with a peracid concentration of at least 10 ppm.

In one aspect of the invention the at least one substrate is an ester substrate selected from the group consisting of methyl lactate, ethyl lactate, methyl glycolate, ethyl glycolate, methyl methoxyacetate, ethyl methoxyacetate, methyl 3-hydroxybutyrate, ethyl 3-hydroxybutyrate, and mixtures thereof.

In another aspect of the invention the at least one substrate is a glyceride substrate selected from the group consisting of monoacetin, diacetin, triacetin, monobutyrin, dibutyrin, tributyrin, glyceryl monooctanoate, glyceryl dioctanoate, glyceryl trioctanoate, and mixtures thereof.

In yet another aspect of the invention the at least one substrate is a glyceride substrate is selected from the group consisting of monoacetin, diacetin, triacetin, and mixtures thereof.

In one aspect of the invention the at least one enzyme catalyst is at least one lipase produced by an organism selected from the genera *Aspergillus, Rhizopus, Penicillium, Candida, Pseudomonas, Mucor, Thermomyces, Alcaligenes,* and *Sus*.

In another aspect the enzyme catalyst is at least one lipase selected from the group consisting of *Candida antartica* lipase B and *Aspergillus niger* lipase.

In another aspect of the invention the at least one enzyme catalyst is at least one protease with perhydrolytic activity and prion-degrading activity.

In another aspect of the invention the enzyme catalyst includes at least one lipase and at least one prion-degrading protease.

In many aspects of the invention the peracid produced by combination of the reaction components is peracetic acid.

Another aspect of the invention provides a method for disinfecting a locus having a concentration of microorganisms or viruses or combinations thereof, said method comprising:
a) providing a set of peracid reaction components, said components comprising:
1. at least one substrate selected from the group consisting of:

i) esters having the structure

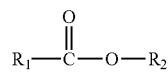

wherein $R_1$=C1 to C10 straight chain or branched chain alkyl optionally substituted with an hydroxyl or a C1 to C4 alkoxy group and $R_2$=C1 to C10 straight chain or branched chain alkyl group, $(CH_2CH_2\text{—}O)_nH$ or $(CH_2CH(CH_3)\text{—}O)_nH$ and n=1 to 10;
ii) glycerides having the structure

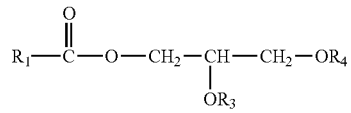

wherein $R_1$=C1 to C10 straight chain or branched chain alkyl optionally substituted with an hydroxyl or a C1 to C4 alkoxy group and $R_3$ and $R_4$ are individually H or $R_1C(O)$; and
iii) amides having the structure:

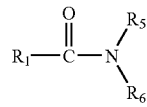

wherein $R_5$ and $R_6$=H or a C1 to C5 straight chain or branched alkyl group;
2) a source of peroxygen that provides a concentration of at least 500 mM hydrogen peroxide upon combining said reaction components; and
3) at least one enzyme catalyst having perhydrolase activity, wherein said enzyme catalyst is selected from the group consisting of lipases, esterases, proteases, and mixtures thereof;
b) combining said reaction components at a pH of 2.5 to 7.5, whereby a concentrated aqueous peracid solution is formed having a peracid concentration of at least 10 ppm within at least about 5 minutes to about 2 hours of combining said reaction components;
c) optionally diluting the said aqueous peracid solution; and
d) contacting said locus with the aqueous peracid solution produced in step b) or step c) whereby the concentration of said microorganisms is reduced at least 3-log.

In another aspect of the invention the locus is contacted with the aqueous peracid solution produced in step b) or step c) as described above, within about 48 hours of combining said reaction components, or within about 5 minutes to about 48 hours.

Another aspect of the invention provides a method for decontaminating or disinfecting a locus contaminated with one or more pathogens including an infective prion or prion particle comprising
a) providing a set of peracid reaction components, said components comprising:
1) at least one substrate selected from the group consisting of:

i) esters having the structure

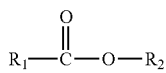

wherein $R_1$=C1 to C10 straight chain or branched chain alkyl optionally substituted with an hydroxyl or a C1 to C4 alkoxy group and $R_2$=C1 to C10 straight chain or branched chain alkyl group, $(CH_2CH_2-O)_nH$ or $(CH_2CH(CH_3)-O)_nH$ and n=1 to 10;

ii) glycerides having the structure

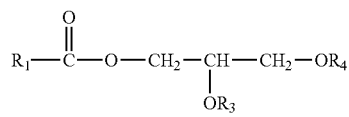

wherein $R_1$=C1 to C10 straight chain or branched chain alkyl optionally substituted with an hydroxyl or a C1 to C4 alkoxy group and $R_3$ and $R_4$ are individually H or $R_1C(O)$; and iii) amides having the structure:

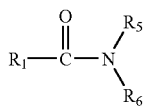

wherein $R_5$ and $R_6$=H or a C1 to C5 straight chain or branched alkyl group;

2) a source of peroxygen that provides a concentration of at least 500 mM hydrogen peroxide upon combining said reaction components; and 3) at least one enzyme catalyst having perhydrolase activity, wherein said enzyme catalyst is selected from the group consisting of lipases, proteases, and mixtures thereof;

4) at least one prion-degrading protease wherein one or more of the prion-degrading proteases may be the same as the enzyme catalyst providing the perhydrolase activity in (a)(3);

b) combining said reaction components at a pH of 2.5 to 7.5, whereby a concentrated peracid solution is produced having a peracid concentration of at least 10 ppm within at least about 5 minutes to about 2 hours of combining said reaction components; and c) optionally diluting said peracid solution produced in step (b).

d) contacting a locus contaminated with a microorganism, a virus, a prion or prion particle, or a combination thereof with the aqueous peracid solution produced in step b) or step c) whereby said locus is disinfected and said prion particle is degraded.

Another aspect of the invention provides a concentrated peracid solution produced in situ by the process described above, wherein said solution includes at least one protease suitable for prion degradation.

Yet another aspect of the invention provides a multifunctional disinfectant composition comprising the concentrated peracid solution produced by the process described above, wherein said composition is suitable for prion degradation, use as a biocide, use as a virucide, or combinations thereof.

DETAILED DESCRIPTION OF THE INVENTION

The stated problems have been solved by the discovery of a combination of enzymes and carboxylic acid esters or amides that, in the presence of an inorganic source of peroxygen (for example, hydrogen peroxide), produce concentrations of peracids sufficient for disinfection or bleaching applications. It was unexpected that concentrations of hydrogen peroxide of from about 500 mM to about 2500 mM could be employed in enzyme-catalyzed perhydrolysis reactions to generate peracid in concentrations of as high as 5000 ppm in 5-10 minutes, where these high peroxide concentrations were expected to rapidly inactivate the perhydrolytic enzyme catalyst.

When compared to the concentrations of peracids produced by the enzymatic perhydrolysis of esters previously reported, the combination of the present enzymes and enzyme substrates in the concentration ranges reported herein unexpectedly and efficiently produced an aqueous solution of peracid at a sufficiently-high concentration to act as a biocidal and virucidal disinfectant, as well as a bleaching agent. Concentrations of peracids in excess of 10 ppm (generally greater than about 75 ppm) were produced as described herein using enzyme catalysts (e.g., lipases, proteases), where the resulting peracid-containing solution, or a dilution thereof, can effect a 5-log or 6-log reduction in infectious bacteria in 5 minutes to 10 minutes at about 25° C.

PCT Publication No. WO2004039418 A1 and U.S. Patent Appln. Pub. No. 20020172989 A1 describe methods for the decontamination of prions that employ a protease or mixture of proteases to destroy the infectious prion protein. In another aspect of the invention, cleaning and disinfecting compositions are provided comprising prion-degrading proteases in combination with in situ generated peracid concentrations having biocidal and/or virucidal activity. In yet another aspect, the prion-degrading proteases (e.g., Proteinase K, Pronase, and combinations thereof) are capable of catalyzing the perhydrolysis of esters and/or amides to produce the corresponding peracid at concentrations efficacious for disinfection, thereby creating a biocide and/or virucide having prion-degrading activity. In a further aspect of the invention, prion-degrading proteases may be used in combination with an added enzyme having perhydrolytic activity, such as a lipase, at a pH where the protease(s) alone may not produce an efficacious concentration of peracid (e.g., at pH of from 4.0 to 6.5). This combination may also yield a synergistic concentration of peracid, where the peracid is produced in a concentration that is greater than the sum of peracid produced by either protease or lipase alone.

Unless otherwise stated, all references cited are hereby specifically incorporated by reference. Further, when an amount, concentration, or other value or parameter is given either as a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

In this disclosure, a number of terms and abbreviations are used. The following definitions apply unless specifically stated otherwise.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, preferably with 5% of the reported numerical value.

As used herein, the term "comprising" means the presence of the stated features, integers, steps, or components as referred to in the claims, but that it does not preclude the presence or addition of one or more other features, integers, steps, components or groups thereof.

As used herein, the term "peracid" is synonymous with peroxyacid, peroxy acid, percarboxylic acid and peroxoic acid. As is commonly known, peracid includes peracetic acid.

As used herein, the term "peracetic acid" is abbreviated as "PAA" and is synonymous with peroxyacetic acid, ethaneperoxoic acid and all other synonyms of CAS Registry Number 79-21-0.

The term "triacetin" is synonymous with glycerin triacetate; glycerol triacetate; glyceryl triacetate, 1,2,3-triacetoxypropane, 1,2,3-propanetriol triacetate and all other synonyms of CAS Registry Number 102-76-1.

As used herein, the term "suitable enzymatic reaction mixture" refers to the materials and water in which the reactants and enzyme catalyst come into contact. The components of the suitable aqueous reaction mixture are provided herein and those skilled in the art appreciate the range of component variations suitable for this process. In one embodiment, the suitable enzymatic reaction mixture produces peracid in situ upon combining the reaction components. As such, the reaction components may be provided as a multicomponent system wherein one or more of the reaction components remains separated until use. The design of systems for combining multiple active components are known in the art and generally will depend upon the physical form of the individual reaction components. For example, multiple active fluids (liquid-liquid) systems typically uses multichamber dispenser bottles or two-phase systems (U.S. Patent Appln. Pub. No. 2005/0139608; U.S. Pat. No. 5,398,846; U.S. Pat. No. 5,624,634; U.S. Pat. No. 6,391,840; E.P. Patent No. 0807156B1; U.S. Patent Appln. Pub. No. 2005/0008526; and PCT Publication No. WO 00/11713A1) such as found in some bleaching applications wherein the desired bleaching agent is produced upon mixing the reactive fluids. Other forms of multicomponent systems used to generate peracid may include, but are not limited to those designed for one or more solid components or combinations of solid-liquid components, such as powders (e.g., many commercially available bleaching composition, U.S. Pat. No. 5,116,575), multi-layered tablets (U.S. Pat. No. 6,210,639), water dissolvable packets having multiple compartments (U.S. Pat. No. 6,995,125) and solid agglomerates that react upon the addition of water (U.S. Pat. No. 6,319,888).

As used herein, the term "perhydrolysis" is defined as the reaction of a selected substrate with peroxide to form a peracid. Typically, an inorganic peroxide is reacted with the selected substrate in the presence of a catalyst to produce the peracid. As used herein, the term "chemical perhydrolysis" includes perhydrolysis reactions in which a substrate (a peracid precursor) is combined with a source of hydrogen peroxide wherein peracid is formed in the absence of an enzyme catalyst. As used herein, the term "enzymatic perhydrolysis" refers to a perhydrolysis reaction that is assisted or catalyzed by an enzyme generally classified as a hydrolase.

"Carboxylic ester hydrolase" refers to an enzyme that catalyzes the hydrolysis of an ester (E.C. 3.1.1.-). The carboxylic ester hydrolase family includes, but is not limited to lipases (e.g., triacylglycerol lipases [E.C. 3.1.1.3]) and esterases.

"Lipase" refers to an enzyme that catalyzes the hydrolysis of fats into glycerol and fatty acids by hydrolyzing ester bonds (EC 3.1.1.3). Some lipases have been reported to have perhydrolysis activity.

"Esterase" refers to an enzyme that catalyzes the hydrolysis of an ester (EC 3.1.1.-). Some esterases have been reported to have perhydrolysis activity "Protease" refers to an enzyme that catalyzes the hydrolytic breakdown of proteins via hydrolysis of peptide bonds (EC 3.4.-). As described herein, some proteases exhibit perhydrolysis activity.

As used herein, the terms "perhydrolase catalyst" and "at least one suitable enzyme catalyst having perhydrolase activity" refer herein to an enzyme catalyst that is characterized by perhydrolase activity. The enzyme catalyst is selected from the group consisting of lipases, esterases, proteases, and/or mixtures thereof wherein the catalyst has perhydrolysis activity. The enzyme catalyst may be in the form of a whole microbial cell, permeabilized microbial cell(s), one or more cell components of a microbial cell extract, partially purified enzyme, or purified enzyme. As used herein, the term "produced from an organism" is used to describe the source of the suitable catalyst. The enzyme catalyst may be produced from the target organism or may be recombinantly produced in a suitable production host.

As used herein, "one unit of enzyme activity" or "one unit of activity" or "U" is defined as the amount of enzyme activity required for the production of 1 μmol of peracid product per minute at a specified temperature.

As used herein, the term "perhydrolase activity" refers to the enzyme activity per unit mass (for example, milligram) of protein, solid or liquid enzyme-containing composition, dry cell weight, or immobilized catalyst weight. Comparisons of perhydrolase activity of catalysts were determined proportional to the dry cell weight, solid or liquid enzyme-containing composition or protein catalyst weight.

As used herein, the term "disinfect" refers to the process of cleansing so as to destroy or prevent the growth of pathogenic microorganisms. As used herein, the term "disinfectant" refers to an agent that disinfects by destroying, neutralizing, or inhibiting the growth of disease-carrying microorganisms. Typically disinfectants are used to treat inanimate objects or surfaces. As used herein, the term "antiseptic" refers to a chemical agent that inhibits the growth of disease-carrying microorganisms.

As used herein, the term "virucide" refers to an agent that inhibits or destroys viruses. An agent that exhibits the ability to inhibit or destroy viruses is described as having "virucidal" activity. Peracids can have virucidal activity. Typical alternative virucides known in the art which may be suitable for use with the present invention include, for example, alcohols, ethers, chloroform, formaldehyde, phenols, beta propiolactone, iodine, chlorine, mercury salts, hydroxylamine, ethylene oxide, ethylene glycol, quaternary ammonium compounds, enzymes, and detergents As used herein, the term "biocide" refers to a chemical agent, typically broad spectrum, which inactivates or destroys microorganisms. A chemical agent that exhibits the ability to inactivate or destroy microorganisms is described as having "biocidal" activity. Peracids can have biocidal activity. Typical alternative biocides known in the art, which may be suitable for use in the present invention include, for example, chlorine, chlorine dioxide, chloroisocyanurates, hypochlorites, ozone, acrolein, amines, chlorinated phenolics, copper salts, organo-sulphur compounds, and quaternary ammonium salts.

As used herein, the phrase "minimum biocidal concentration" refers to the minimum concentration of a biocidal agent that, for a specific contact time, will produce a desired lethal, irreversible reduction in the viable population of the targeted microorganisms. The effectiveness can be measured by the $log_{10}$ reduction in viable microorganisms after treatment. In one aspect, the targeted reduction in viable cells after treatment is a 3-log reduction, more preferably a 4-log reduction, and most preferably at least a 5-log reduction. In another aspect, the minimum biocidal concentration is a 6-log reduction in viable microbial cells-.

As used herein, the terms "prion", "prion particle", and "infection prion particle" refer to infectious proteins associated with neurodegenerative diseases including, but not limited to scrapie, bovine spongiform encephalopathy (BSE), trasmissible spongiform encephalopathy (TSE), chronic wasting disease, and Creutzfedit-Jacob disease. The term "prion-destructive protease" or "prion-degrading protease" refers to at least one protease (preferably combinations of two or more proteases) useful for degrading or destroying infectious prion particles (for example, see WO 2004039418 A1 and US 20020172989 A1). In one embodiment, the prion-destructive protease is selected from Proteinase K, Pronase, and mixtures thereof. In a preferred embodiment, the prion-destructive protease is a mixture of Proteinase K and Pronase.

In one aspect, the peracids formed by the present process can be used to reduce a microbial population when applied on and/or at a locus. As used herein, a "locus" of the invention comprises part or all of a target surface suitable for disinfecting or bleaching. Target surfaces include all surfaces that can potentially be contaminated with microorganisms, viruses, prions or combinations thereof. Non-limiting examples include equipment surfaces found in the food or beverage industry (such as tanks, conveyors, floors, drains, coolers, freezers, equipment surfaces, walls, valves, belts, pipes, drains, joints, crevasses, combinations thereof, and the like); building surfaces (such as walls, floors and windows); non-food-industry related pipes and drains, including water treatment facilities, pools and spas, and fermentation tanks; hospital or veterinary surfaces (such as walls, floors, beds, equipment, (such as endoscopes) clothing worn in hospital/veterinary or other healthcare settings, including scrubs, shoes, and other hospital or veterinary surfaces); restaurant surfaces; bathroom surfaces; toilets; clothes and shoes; surfaces of barns or stables for livestock, such as poultry, cattle, dairy cows, goats, horses and pigs; and hatcheries for poultry or for shrimp. Additional surfaces also include food products, such as beef, poultry, pork, vegetables, fruits, seafood, combinations thereof, and the like. The locus can also include water absorbent materials such as infected linens or other textiles. The locus also includes harvested plants or plant products including seeds, corns, tubers, fruit, and vegetables, growing plants, and especially crop growing plants, including cereals, leaf vegetables and salad crops, root vegetables, legumes, berried fruits, citrus fruits and hard fruits.

Non-limiting examples of surface materials are metals (e.g., steel, stainless steel, chrome, titanium, iron, copper, brass, aluminum, and alloys thereof), minerals (e.g., concrete), polymers and plastics (e.g., polyolefins, such as polyethylene, polypropylene, polystyrene, poly(meth)acrylate, polyacrylonitrile, polybutadiene, poly(acrylonitrile, butadiene, styrene), poly(acrylonitrile, butadiene), acrylonitrile butadiene; polyesters such as polyethylene terephthalate; and polyamides such as nylon),. Additional surfaces include brick, tile, ceramic, porcelain, wood, vinyl, linoleum, and carpet.

Suitable Aqueous Reaction Conditions for the Enzyme-catalyzed Preparation of Peracids from Carboxylic Acid Esters and/or Amides and Hydrogen Peroxide A process is provided to produce an aqueous mixture comprising a peracid by reacting a suitable substrate, at least one enzyme catalyst having perhydrolysis activity, and a source of peroxygen providing a hydrogen peroxide concentration of 500 mM or more at a neutral to acidic pH. As used herein, the terms "peroxygen source" and "source of peroxygen" refer to compounds capable of providing hydrogen peroxide at a concentration of about 500 mM or more when in an aqueous solution including, but not limited to hydrogen peroxide, hydrogen peroxide adducts, perborates, and percarbonates. As described herein, the peroxygen source is capable of providing, upon combining the reaction components, a mixture having a hydrogen peroxide concentration of at least 500 mM.

As used herein, the terms "suitable substrate", "peracid precursor", and "bleach activator" will be used to describe substrates capable of undergoing enzymatic perhydrolysis to generate a peracid using the present reaction conditions. The substrates may also undergo partial chemical perhydrolysis in the presence or absence of enzyme. As such, substrates suitable in the present invention are those that can undergo enzymatic perhydrolysis to generate at least 10 ppm more peracid then that produced chemically under identical reaction conditions, preferably at least 100 ppm, more preferably at least 250 ppm, even more preferably at least 500 ppm, yet even more preferably at least 1000 ppm, still even more preferably at least 2000 ppm, and most preferably at least 5000 ppm peracid.

Suitable substrates may include one or more carboxylic acid esters, amides, glycerides (mono-, di-, and/or triglycerides) or mixture thereof capable of undergoing enzymatic perhydrolysis under the present reaction conditions. In one embodiment, the substrate may be optionally substituted, especially with alkoxy and/or hydroxyl groups. In another embodiment, the substrate may be a acylated polyol. In yet another embodiment, the acylated polyol is selected from the group consisting of mono-, di- or polyacylated polyols derived from glycerol, erythritol, threitol, xylitol, ribitol, arabitol, mannitol, and sorbitol.

In a preferred embodiment, suitable substrates include carboxylic acid esters, amides, and/or glycerides having a formula selected from the group consisting of:

a) esters of the formula

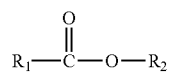

wherein $R_1$=C1 to C10 strain chain or branched chain alkyl optionally substituted with an hydroxyl or a C1 to C4 alkoxy group and $R_2$=C1 to C10 strain chain or branched chain alkyl group, $(CH_2CH_2-O)_nH$ or $(CH_2CH(CH_3)-O)_nH$ and n=1 to 10;

b) glycerides of the formula

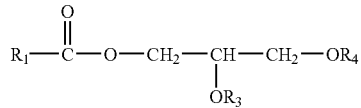

wherein $R_1$=C1 to C10 straight chain or branched chain alkyl optionally substituted with an hydroxyl or a C1 to C4 alkoxy group and $R_3$ and $R_4$ are individually H or $R_1C(O)$; and c) amides of the formula

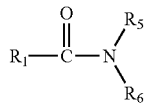

wherein $R_5$ and $R_6$=H or a C1 to C5 straight chain or branched alkyl group. In one embodiment, the substrate may be a mixture of one or more suitable substrates as described herein.

In a preferred embodiment, the substrates are selected from the group consisting of methyl lactate, ethyl lactate, methyl glycolate, ethyl glycolate, methyl methoxyacetate, ethyl methoxyacetate, methyl 3-hydroxybutyrate, ethyl 3-hydroxybutyrate, triethyl 2-acetyl citrate, glucose pentaacetate, gluconolactone, monoacetin, diacetin, triacetin, monobutyrin, dibutyrin, tributyrin, glyceryl monooctanoate, glyceryl dioctanoate, glyceryl trioctanoate, acetamide, diacetamide, and mixtures thereof.

In yet a further preferred embodiment, the substrate is selected from the group consisting of monoacetin, diacetin, triacetin, acetamide, diacetamide, and mixtures thereof.

The enzyme substrate is present in the reaction mixture at a concentration sufficient to produce the desired concentration of peracid upon enzyme-catalyzed perhydrolysis. It has been demonstrated in the accompanying examples that there are preferred combinations of enzyme substrate and enzyme catalyst that produce a desirable concentration of peracid. The substrate need not be completely soluble in the reaction mixture, but have sufficient solubility to permit conversion of the ester or amide by the enzyme catalyst to the corresponding peracid. The substrate is present in the reaction mixture at a concentration of 0.05 wt % to 40 wt % of the reaction mixture, preferably at a concentration of 0.1 wt % to 20 wt % of the reaction mixture, and more preferably at a concentration of 0.5 wt % to 10 wt % of the reaction mixture. Preferred substrates when using a lipase, esterase, or protease as catalyst, or combinations of lipases and/or proteases as catalyst, include monoacetin, diacetin, triacetin, and mixtures of monoacetin/diacetin/triacetin. Additional preferred substrates when using a protease as catalyst, or combinations of lipases and proteases as catalyst, include acetamide, diacetamide, and mixtures thereof.

The peroxygen source may include, but is not limited to, hydrogen peroxide, perborate salts (e.g., sodium perborate) and percarbonate salts (e.g. sodium percarbonate). The concentration of peroxygen compound in the reaction mixture may range from 0.1 wt % to about 50 wt %, preferably from 1 wt % to about 40 wt %, more preferably from 2 wt % to about 30 wt %.

The concentration of the hydrogen peroxide provided by the peroxygen compound in the aqueous reaction mixture is initially at least 500 mM or more upon combining the reaction components. In one embodiment, the hydrogen peroxide concentration in the aqueous reaction mixture is 1000 mM or more. In another embodiment, the hydrogen peroxide concentration in the aqueous reaction mixture is 2500 mM or more.

The molar ratio of the hydrogen peroxide to substrate ($H_2O_2$:substrate) in the aqueous reaction mixture may be from about 0.1 to 20, preferably about 0.5 to 10, and most preferably about 2 to 5.

The reaction components may be combined in individual batches or may be combined using a continuous process.

The enzyme catalyst is chosen from the class of hydrolytic enzymes that includes esterases, lipases and proteases (EC 3.1.1.-, EC 3.1.1.3, and EC 3.4.-.-, respectively). In particular, the enzymes that are useful in the present invention are hydrolytic enzymes, such as esterases, lipases, and proteases, whose catalytic activity is normally the hydrolysis of an ester to the corresponding carboxylic acid and alcohol, or the hydrolysis of an amide to the corresponding carboxylic acid and ammonia or amine, where in the presence of hydrogen peroxide (or a functionally-equivalent peroxygen containing compound) the ester or amide is subject to an enzyme-catalyzed perhydrolysis, producing the corresponding percarboxylic acid.

In one aspect, the enzyme catalyst is a lipase derived from a eukaryotic or prokaryotic organism. In another aspect, the lipase is derived from an organism selected from the genera consisting of *Aspergillus, Rhizopus, Penicillium, Candida, Pseudomonas, Mucor, Thermomyces, Alcaligenes*, and *Sus*. In a preferred aspect, the source of the lipase is selected from the group consisting of *Aspergillus niger, Rhizopus oryzae, Penicillium* sp. I, *Penicillium* sp. II, *Candida rugosa, Candida antartica* lipase A, *Candida antartica* lipase B, *Pseudomonas cepacia, Pseudomonas fluorescens, Thermomyces languinosus, Mucor miehei, Sus scrofa*, and *Alcaligenes* sp. In a further preferred aspect, the lipase is selected from the group consisting of *Aspergillus* sp. lipase, *Aspergillus niger* lipase, *Candida antartica* lipase B, *Pseudomonas* sp. lipase, *Alcaligenes* sp. lipase, *Candida rugosa* lipase, *Rhizopus oryzae* lipase, and mixtures thereof. Many of the lipases of exemplified herein were obtained from BioCatalytics Inc. (Pasadena, Calif.) and referred to by their corresponding catalog number (Example 1, Table 1). Accordingly, in a further preferred aspect, the lipase is selected from the group consisting of ICR-101 *Aspergillus* sp. lipase, ICR-102 *Rhizopus* sp. lipase, ICR-103 *Rhizopus oryzae* lipase, ICR-104 *Penicillium* sp. I lipase, ICR-105 *Penicillium* sp. II lipase, ICR-106 *Candida rugosa* lipase, ICR-107 *Pseudomonas cepacia* lipase, ICR-108 *Pseudomonas* sp. lipase, ICR-109 *Pseudomonas fluorescens* lipase, ICR-110 *Candida antartica* lipase B, ICR-111 *Candida* sp. lipase, ICR-112 *Candida antartica* lipase A, ICR-113 *Pseudomonas* sp. lipase, ICR-114 porcine pancreas lipase, ICR-115 *Thermomyces languinosus* lipase, ICR-116 *Mucor miehei* lipase, and ICR-117 *Alcaligenes* sp. lipase. In a further preferred aspect, the lipase is selected from the group consisting of Lipase AY "Amano" 30 (*Candida rugosa* lipase), Lipase R "Amano" (*Penicillium roqueforti* lipase), Lipase F-AP15 (*Rhizopus oryzae* lipase), Lipase M "Amano" 10 (*Mucor javanicus* lipase), Lipase A "Amano" 12 (*Aspergillus niger* lipase), Lipase G "Amano" 50 (*Penicillium camembertii* lipase), Amano F-DS lipase (*Rhizopus oryzae* lipase), Amano DS lipase (*Aspergillus niger* lipase) (all from Amano), and CALB L (liquid formulation of *Candida antartica* lipase B), Novozym 435 (immobilized *Candida antartica* lipase B), Lipozyme TL (*Thermomyces lanuginosus* lipase), Palatase 20000L (*Aspergillus oryzae* lipase) (all from Novozymes), and Validase AN lipase (*Aspergillus niger* lipase), Dietrenz CR lipase (*Candida rugosa* lipase) (all from Valley Research), and Enzeco MLC lipase (a microbial lipase concentrate from *Aspergillus niger* sold by Enzyme Development Corporation. Most preferably, the lipase is selected form the group consisting of BioCatalytics ICR-101 (*Aspergillus* sp. lipase), BioCatalytics ICR-110 (*Candida antartica* lipase B),BioCatalytics Chirazyme L2 lipase (*C. antartica* lipase B), BioCatalytics ICR-113 (*Pseudomonas* sp. lipase), BioCatalytics CR-117 (*Alcaligenes* sp. lipase), Lipase A "Amano" 12 (*Aspergillus niger* lipase), Novozym CALB L (*Candida antartica* lipase B), Novozym 435 (immobilized *Candida antartica* lipase B), Novozym Palatase 20000L (*Aspergillus oryzae* lipase), and Valley Research Validase AN (*Aspergillus niger* lipase).

In one embodiment, the enzyme catalyst is a protease (E.C. 3.4.-.-) derived from a eukaryotic or prokaryotic organism. In another embodiment the protease is derived from an organism selected from the genera consisting of *Aspergillus, Rhizopus, Bacillus, Sus, Carica, Ananas, Pseudomonas, Mucor, Thermomyces, Alcaligenes*, and *Sus*. In a preferred aspect, the source of the lipase is selected from the group consisting of *Aspergillus saitoi, Rhizopus* sp, *Bacillus* sp., *Bacillus subtilis, Sus scrofa* (pig), *Carica papaya* (papaya), *Ananas comosus* (pineapple), *Streptomyces griseus*, and *Tritirachium album*. In a preferred embodiment, the protease is selected from the group consisting of the *Aspergillus saitoi* type XIII protease, *Rhizopus* sp. type XVIII protease, *Bacillus* sp. protease, *Sus scrofa* pepsin, *Carica papaya* Chymopapain, *Ananas comosus* bromelain, *Carica papaya* papain, *Streptomyces griseus* Pronase (also known as Pronase E®), *Tritirachium album* Proteinase K (including recombinantly produced Proteinase K from *Pichia pastoris*), and mixtures thereof.

Many enzyme catalysts (whole cell, partially purified, or purified) have been reported to have catalase activity (EC 1.11.1.6). Catalases catalyze the conversion of hydrogen peroxide into oxygen and water. In a preferred embodiment, the enzyme catalyst lacks significant catalase activity or is engineered or purified to decrease or eliminate catalase activity.

The concentration of enzyme catalyst employed in the aqueous reaction mixture depends in part on the specific catalytic activity of the enzyme catalyst, and is chosen to obtain the desired rate of reaction. The weight of soluble enzyme used as catalyst in perhydrolysis reactions typically ranges from 0.01 mg to 10 mg of enzyme per mL of total reaction volume, preferably from 0.10 mg to 2.0 mg of enzyme per mL. The enzyme may also be immobilized on a soluble or insoluble support using methods well-known to those skilled in the art; see for example, *Immobilization of Enzymes and Cells*; Gordon F. Bickerstaff, Editor; Humana Press, Totowa, N.J., USA; 1997. The use of immobilized enzymes permits the recovery and reuse of the catalyst in subsequent reactions. Additional forms of the enzyme catalyst that are useful in the present application include whole microbial cells, cell extracts, and partially-purified enzymes. These additional forms of the catalyst may also be immobilized using the methods referenced above.

In one aspect, the concentration of peracid generated by the combination of chemical perhydrolysis and enzymatic perhydrolysis of the substrate is sufficient to provide an effective concentration of peracid for bleaching or disinfection at a desired pH. In another aspect, the present methods provide combinations of enzymes and enzyme substrates to produce the desired effective concentration of peracid, where, in the absence of added enzyme, there is a significantly lower concentration of peracid produced. Although there may in some cases be substantial chemical perhydrolysis of the enzyme substrate by direct chemical reaction of inorganic peroxide with the enzyme substrate, there may not be a sufficient concentration of peracid generated to provide an effective concentration of peracid in the desired applications, and a significant increase in total peracid concentration is achieved by the addition of an appropriate enzyme catalyst to the reaction mixture.

The present process produces a concentrated aqueous peracid solution that may be optionally diluted (e.g., with water) prior to use. As used herein, "peracid solution", "aqueous peracid solution", and "concentrated aqueous peracid solution" will refer to the concentrated peracid solution generated by the present enzyme-catalyzed perhydrolysis process. In one embodiment, the "concentrated aqueous peracid solution" comprises at least 10 ppm peracid, preferably at least 100 ppm peracid, more preferably at least 200 ppm peracid, even more preferably at least 250 ppm peracid, yet even more preferably at least 500 ppm, still yet even more preferably at least 1000 ppm, yet even more preferably at least 2000 ppm, and most preferably at least 5000 ppm. The product mixture comprising the peracid may be optionally diluted with water, or a solution predominantly comprised of water, to produce a mixture with the desired lower concentration of peracid. The decision to dilute the aqueous peracid solution produced by the present method will depend upon a variety of factors including, but not limited to the target application (animal health disinfectant, instrument sterilization, household cleaner, bleaching agent, etc.), temperature and time required to ensure the desired level efficacy for the target application, the amount of soil at and/or on the target locus, and the target pathogen's susceptibility to peracid disinfectants. The reaction time required to produce the desired concentration of peracid is not greater than about two hours, preferably not greater than about 30 minutes, more preferably not greater than about 10 minutes, and most preferably less than or about 5 minutes. As the reaction continues, the concentration of peracid will increase to the point of equilibrium. As such, the present invention is directed to a process that produces a high concentration within about 5 minutes, said concentration may continue to rise until an equilibrium of the reaction is reached.

The temperature of the peracid synthesis reaction is chosen to control both the reaction rate and the stability of the enzyme catalyst activity. The temperature of the reaction may range from just above the freezing point of the reaction mixture (approximately 0° C.) to about 65° C., with a preferred range of reaction temperature of from about 5° C. to about 35° C.

The pH of the final reaction mixture (i.e., pH of the reaction mixture upon combining the reaction components) containing peracid is 2.5 to 7.5, preferably from 3 to 7, more preferably from 3.5 to 6.5, and most preferably 4 to 6.5. The pH of the reaction, and of the final reaction mixture, may optionally be controlled by the addition of a suitable buffer, including, but not limited to phosphate, pyrophosphate, bicarbonate, acetate, or citrate. The concentration of buffer is from 0.1 mM to 1.0 M, preferably from 1 mM to 100 mM, most preferably from 10 mM to 50 mM.

In another aspect, the enzymatic perhydrolysis product may contain additional components that provide desirable functionality. These additional components include, but are not limited to detergent builders, emulsifiers, surfactants, corrosion inhibitors, enzyme stabilizers, and peroxide stabilizers (e.g., metal ion chelating agents). Many of the additional components are well know in the detergent industry (see for example U.S. Pat. No. 5,932,532 hereby incorporated by reference). Examples of emulsifiers include polyvinyl alcohol or polyvinylpyrrolidine. Examples of surfactants, including a) non-ionic surfactants such as block copolymers of ethylene oxide or propylene oxide, ethoxylated or propoxylated linear and branched primary and secondary alcohols, and aliphatic phosphine oxides b) cationic surfactants such as such as quaternary ammonium compounds, particularly quaternary ammonium compounds having a C8-C20 alkyl group bound to a nitrogen atom additionally bound to three C1-C2 alkyl groups, c) anionic surfactants such as alkane carboxylic acids (e.g., C8-C20 fatty acids), alkyl phosphonates, alkane sulfonates (e.g., sodium dodecylsulphate "SDS") or linear or branched alkyl benzene sulfonates, alkene sulfonates and d) amphoteric and zwitterionic surfactants such as aminocarboxylic acids, aminodicarboxylic acids, and alkybetaines. Additional components may include fragrances, dyes, stabilizers of hydrogen peroxide (e.g., 1-hydroxyethylidene -1,1-diphosphonic acid (Dequest 2010, Solutia Inc., St. Louis, Mo.)), stabilizers of enzyme activity (e.g., polyethyleneglycol (PEG)), detergent builders and metal chelators (e.g., ethylenediaminetetraacetic acid (EDTA)).

Enzymatic in Situ Production of Peracids

The present aqueous enzymatic method produces high concentrations of peracid or peracids in situ. The peracids produced are quite reactive and relatively unstable, generally decreasing in concentration over time. As such, it may be desirable to keep the various reaction components separated, especially for liquid formulations. In one aspect, the hydrogen peroxide source is separate from either the substrate or the enzyme, preferably from both. This can be accomplished using a variety of techniques including, but not limited to the use of multicompartment chambered dispensers (U.S. Pat. No. 4,585,150) and physically combining the enzyme catalyst with the present substrates and hydrogen peroxide source to initiate the aqueous enzymatic perhydrolysis reaction. The enzyme catalyst may be immobilized within the body of the reaction chamber or separated (e.g. filtered, etc.) from the reaction product comprising the peracid prior to contacting the surface and/or object targeted for treatment. The enzyme catalyst may be in a liquid matrix or in a solid form (i.e. powdered, tablet) or embedded within a solid matrix that is subsequently mixed with the substrates and hydrogen peroxide source to initiate the enzymatic perhydrolysis reaction. In a further aspect, the enzyme catalyst may be contained within a dissolvable or porous pouch that may be added to the aqueous substrate matrix to initiate enzymatic perhydrolysis.

HPLC Assay Method for Determining the Concentration of Peracid and Hydrogen Peroxide.

A variety of analytical methods can be used in the present method to analyze the reactants and products including, but not limited to titration, high performance liquid chromatography (HPLC), gas chromatography (GC), mass spectroscopy (MS), and capillary electrophoresis (CE).

The analytical procedure described by U. Karst et al. (*Anal. Chem.*, 69 (17):3623-3627 (1997)) was employed, as described herein, for analysis of product mixtures containing peracid and hydrogen peroxide. Briefly, the concentration of peracetic acid (PAA) in analyzed samples ranged from 0.025 mM-10 mM, and the concentration of $H_2O_2$ ranged from 0.075 mM-3 mM. Reaction mixtures containing peracid and/or hydrogen peroxide were, if necessary prior to analysis, diluted to produce a concentration of peracid or peroxide in these ranges. Into a 4-mL vial was placed 0.100 mL of 20 mM methyl p-tolyl sulfide (MTS) in acetonitrile, 0.300 mL of distilled and deionized water (dd) and 0.100 mL of sample solution (undiluted or diluted with dd water by a factor of up to 1:25 for analysis of peracid), or 0.100 mL of 20 mM MTS in acetonitrile and 0.390 mL of dd water were added to 0.010 mL of a 1:10 dilution of sample solution (for analysis of hydrogen peroxide). After a reaction time of 10 minutes (in the dark, with no stirring), 0.400 mL $CH_3CN$ and 0.100 mL of 40-mM triphenylphosphine (TPP) in $CH_3CN$ were added to start the second derivatization reaction for detection of peroxide. The solution was left standing in the dark for 30 min to complete the assay reaction. At the end of 30 minutes, 0.100 mL of 10 mM N,N-diethyl-m-toluamide (DEET, HPLC external standard) was added and the resulting solution analyzed by HPLC: Supelco Discovery C8 10-cm column with pre-column, 10-μL injection, UV detection at 225 nm, solvent A: acetonitrile, solvent B: deionized water, 1 mL/min gradient as follows:

| Time (min:sec) | % $CH_3CN$ | % $H_2O$ |
|---|---|---|
| 0:00 | 40 | 60 |
| 3:00 | 40 | 60 |
| 3:10 | 100 | 0 |
| 4:00 | 100 | 0 |
| 4:10 | 40 | 60 |
| 7:00 (stop) | 40 | 60 |

Determination of Minimum Biocidal Concentration of Peracids

The method described by J. Gabrielson, et al. (*J. Microbiol. Methods* 50: 63-73 (2002)) was employed for determination of the Minimum Biocidal Concentration (MBC) of peracids, or for determination of the MBC of hydrogen peroxide and enzyme substrates. The assay method is based on XTT reduction inhibition, where XTT ((2,3-bis[2-methoxy4-nitro-5-sulfophenyl]-5-[(phenylamino)carbonyl]-2H-tetrazolium, inner salt, monosodium salt) is a redox dye that indicates microbial respiratory activity by a change in optical density (OD) measured at 490 nm or 450 nm. However, there are a variety of other methods available for testing the activity of disinfectants and antiseptics including, but not limited to viable plate counts, direct microscopic counts, dry weight, turbidity measurements, absorbance, and bioluminescence (see, for example Brock, Semour S., *Disinfection, Sterilization, and Preservation*, 5$^{th}$ edition, Lippincott Williams & Wilkins, Philadelphia, Pa., USA; 2001).

Determination of Virucidal Activity for Disinfectants and Antiseptics

Methods to evaluate the virucidal activity of disinfectants and antiseptics are well known in the art (Brock, S., supra and Papageorgiou et al., *Appl. Environ. Microbiol.*, 67(12):5844-5848 (2001)). The present peracid compositions are expected to exhibit virucidal activity. It has been reported that acidic conditions (pH <7) may enhance virucidal activity. Accordingly, in a further aspect, the present peracid composition may be comprised of an acidic pH (pH <7). In another embodiment, the pH is less than 6.5, preferably less than 6, more preferably less than about 5.

Uses of Enzymatically Prepared Peracid Compositions

The enzyme-generated peracid produced according to the present methods can be used in a variety of applications for reduction of microbial, fungal, viral, and infectious protein (i.e., prion) contamination at a locus as defined herein, such as for the decontamination of medical instruments (e.g., endoscopes), textiles (e.g., garments, carpets), food preparation surfaces, food storage and food-packaging equipment, materials used for the packaging of food products, chicken hatcheries and grow-out facilities, animal enclosures, water treatment facilities, pools and spas, fermentation tanks, and spent process waters that have microbial and/or virucidal activity. In a preferred aspect, the present peracid compositions are particularly useful as a cleaning and disinfecting agent for non-autoclavable medical instruments and food packaging equipment. As the peracid-containing formulation may be prepared using GRAS or food-grade components (enzyme, enzyme substrate, hydrogen peroxide, and buffer), the enzyme-generated peracid may also be used for decontamination of animal carcasses, meat, fruits and vegetables, or for decontamination of prepared foods. The enzyme-generated peracid may be incorporated into a product whose final form is a powder, liquid, gel, solid or aerosol. The enzyme-generated peracid may be diluted to a concentration that still provides an efficacious decontamination.

The compositions comprising an efficacious concentration of peracid can be used to clean and disinfect surfaces and/or objects contaminated (or suspected of being contaminated) with pathogenic microorganisms, viruses, and/or prions by contacting the surface or object with the products produced by the present processes. As used herein, "contacting" refers to placing a disinfecting composition comprising an effective concentration of peracid in contact with a locus suspected of contamination with a disease-causing entity for a period of time sufficient to clean and disinfect. The time, temperature, and effective concentration used when contacting the desired locus can be easily determined by one of skill in the art. Contacting includes spraying, treating, immersing, flushing, pouring on or in, mixing, combining, painting, coating, applying, affixing to and otherwise communicating a peracid solution comprising an efficacious concentration of peracid with the surface or inanimate object suspected of being contaminated.

Peracid Disinfectants Having Prion-degrading Activity

Patent applications PCT Publication No. WO 2004039418 A1 and U.S. Patent Appln. Pub. No. 20020172989 A1 describe methods for the decontamination of prions that employ a protease or mixture of proteases to destroy the infectious prion protein (Langeveld et al., *J. Infect. Diseases*, 188:1782-1789 (2003)). The accompanying examples in the present application also demonstrate that proteases capable of decontaminating infectious prions are capable of catalyzing the perhydrolysis of esters or amides to produce the corresponding peracid at concentrations efficacious for disinfection, thereby making possible the production of a mixture containing both an antimicrobial peracid and prion-degrading protease(s) using a single enzyme system. This composition comprising prion degrading proteases and an efficacious concentration of a peracid may optionally include one or more surfactants and may include a period of heating to aid in prion decontamination. In one embodiment, the concentration of surfactant used when decontaminating prions may range from 0.01 to 50 wt %, preferably 0.1 to 10 wt %. The heat treatment step typically occurs at a temperature of at least 40° C. to 130° C., preferably at least 80° C., and most preferably at least 100° C. The optional heat treatment typically comprises a time of at least 1 minute up to 48 hours, preferably less than 24 hours, and most preferably less than 2 hours. In one embodiment, the method to degrade prions includes both a surfactant and a heat treatment. Additionally, the proteases may be used in combination with an added lipase at a pH where the protease(s) alone may not produce an efficacious concentration of peracid (e.g., at pH 4.0), the use of a synergistic combination of protease and lipase can produce a concentration of peracid greater than the sum of peracid produced by either protease or lipase alone.

The process to decontaminate a locus contaminated with (or at least suspected of being contaminated with) an infectious prion using the present aqueous peracid solutions may additionally include at least one step of treating the locus with a surfactant before or after contacting the locus with the aqueous peracid solution produced by the present process. In another embodiment, the surfactant may optionally be included in the peracid reaction mixture prior to contacting the prion contaminated locus. In yet another embodiment, the present process may optionally include a heat treatment step where the locus is heat treated before, during, or after contacting said locus with the aqueous peracid solution. In still yet another embodiment, the present process may include both the optional heating step and the surfactant treatment step.

General Methods

The following examples are provided to demonstrate preferred aspects of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

All reagents and materials were obtained from DIFCO Laboratories (Detroit, Mich.), GIBCO/BRL (Gaithersburg, Md.), TCI America (Portland, Oreg.), Charkit Chemical Corporation (Darien, Conn.), Eastman Chemical Co. (Kingsport, Tenn.) or Sigma/Aldrich Chemical Company (St. Louis, Mo.) unless otherwise specified. Enzymes were obtained from Sigma/Aldrich Chemical Company (St. Louis, Mo.), Bio-Catalytics (Pasadena, Calif.), Amano Enzymes USA (Lombard, Ill.), Valley Research (South Bend, Ind.), Enzyme Development Corporation (New York, N.Y.), and Novozymes (Franklinton, N.C.).

The abbreviations in the specification correspond to units of measure, techniques, properties, or compounds as follows: "sec" means second(s), "min" means minute(s), "h" or "hr" means hour(s), "d" means density in g/mL, "µL" means microliters, "mL" means milliliters, "L" means liters, "mM" means millimolar, "M" means molar, "mmol" means millimole(s), "wt" means weight, "wt %" means weight percent, "g" means grams, "µg" means micrograms, "HPLC" means high performance liquid chromatography, "O.D." means optical density at the designated wavelength, "dcw" means dry cell weight, "CFU" means colony forming units, "ATCC" means American Type Culture Collection, "U" means units of perhydrolase activity, "RPM" means revolutions per minute, "EDTA" means ethylenediaminetetraacetic acid, "dd" means distilled and deionized, and "DTT" means dithiothreitol.

EXAMPLE 1

Lipase-catalyzed Perhydrolysis of Triacetin at pH 6.5

Into a 4-mL glass vial with stir bar was added 1 mg enzyme (ICR 101-117, BioCatalytics, Pasadena, Calif.) in 0.050 mL of 50 mM potassium phosphate buffer (pH 6.5), 0.900 mL of 278 mM triacetin in 50 mM potassium phosphate buffer (pH 6.5, 250 mM final triacetin concentration), and 0.052 mL 30% hydrogen peroxide (500 mM final concentration). After stirring for 5 or 30 minutes at 22° C., a 0.250 mL sample was filtered using a 30,000 Nominal Molecular Weight Limit (NMWL) filter (Millipore UltraFree-MC, Millipore Corp., Billerica, Mass.) centrifuged for 2 minute at 12,000 RPM. A portion of the filtered reaction samples was diluted 1:10 with dd water and analyzed for hydrogen peroxide, and the remaining portion of the sample was directly analyzed for peracid using the HPLC assay method (Table 1).

TABLE 1

Lipase-catalyzed Perhydrolysis of 250 mM Triacetin at pH 6.5.

| enzyme | enzyme source | peracetic acid (ppm), 5 min | peracetic acid (ppm), 30 min |
|---|---|---|---|
| ICR-101 | *Aspergillus* sp. | 282 | 179 |
| ICR-102 | *Rhizopus* sp. | 80 | 235 |
| ICR-103 | *Rhizopus oryzae* | 113 | 36 |
| ICR-104 | *Penicillium* sp. I | 131 | 142 |
| ICR-105 | *Penicillium* sp. II | 144 | 66 |
| ICR-106 | *Candida rugosa* | 171 | 105 |
| ICR-107 | *Pseudomonas cepacia* | 179 | 0 |
| ICR-108 | *Pseudomonas* sp. | 180 | 30 |
| ICR-109 | *Pseudomonas fluorescens* | 183 | 11 |
| ICR-110 | *Candida antartica* lipase B | 337 | 398 |
| ICR-111 | *Candida* sp. | 238 | 117 |
| ICR-112 | *Candida antartica* lipase A | 134 | 0 |
| ICR-113 | *Pseudomonas* sp. | 241 | 358 |
| ICR-114 | porcine pancreas | 135 | 0 |
| ICR-115 | *T. languinosus* | 216 | 113 |
| ICR-116 | *Mucor miehei* | 238 | 117 |
| ICR-117 | *Alcaligenes* sp. | 293 | 370 |

EXAMPLE 2

Lipase-catalyzed Perhydrolysis of Triacetin at pH 4.0

Into a 4-mL glass vial with stir bar was added 1 mg enzyme (ICR 101-117, BioCatalytics, Pasadena, Calif.) in 0.050 mL of 50 mM sodium acetate/acetic acid buffer (pH 4.0), 0.900 mL of 278 mM triacetin in 50 mM sodium acetate/acetic acid buffer (pH 4.0, 250 mM final triacetin concentration), and 0.052 mL 30% hydrogen peroxide (500 mM final concentration). After stirring for 5 or 30 minutes at 22° C., a 0.250 mL sample was filtered using a 30,000 NMWL filter (Millipore UltraFree-MC) centrifuged for 2 minute at 12,000 RPM. A portion of the filtered reaction samples was diluted 1:10 with dd water and analyzed for hydrogen peroxide, and the remaining portion of the sample was directly analyzed for peracid using the HPLC assay method (Table 2).

TABLE 2

Lipase-catalyzed Perhydrolysis of 250 mM Triacetin at pH 4.0.

| enzyme | enzyme source | peracetic acid (ppm), 5 min | peracetic acid (ppm), 30 min |
|---|---|---|---|
| no enzyme | | 10 | 9.6 |
| ICR-101 | *Aspergillus* sp. | 238 | 555 |
| ICR-102 | *Rhizopus* sp. | 11 | 0 |
| ICR-103 | *Rhizopus oryzae* | 0 | 4 |
| ICR-104 | *Penicillium* sp. I | 9 | 16 |
| ICR-105 | *Penicillium* sp. II | 11 | 19 |
| ICR-106 | *Candida rugosa* | 23 | 34 |
| ICR-107 | *Pseudomonas cepacia* | 32 | 135 |
| ICR-108 | *Pseudomonas* sp. | 33 | 53 |
| ICR-109 | *Pseudomonas fluorescens* | 32 | 68 |
| ICR-110 | *Candida antartica* lipase B | 362 | 688 |
| ICR-111 | *Candida* sp. | 24 | 79 |
| ICR-112 | *Candida antartica* lipase A | 151 | 86 |
| ICR-113 | *Pseudomonas* sp. | 221 | 370 |
| ICR-114 | porcine pancreas | 165 | 53 |
| ICR-115 | *T. languinosus* | 206 | 132 |
| ICR-116 | *Mucor miehei* | 14 | 0 |
| ICR-117 | *Alcaligenes* sp. | 185 | 710 |

EXAMPLE 3

Lipase-catalyzed Perhydrolysis of Triacetin at pH 4.0

Into a 4-mL glass vial with stir bar was added 2 mg enzyme (lipase ICR 101 or ICR 110, BioCatalytics, Pasadena, Calif.) and 1.0 mL of 50 mM sodium acetate/acetic acid buffer (pH 4.0) containing from 250 mM or 500 mM triacetin and 500 mM or 2500 mM hydrogen peroxide). After stirring for 5 or 30 minutes at 23° C., a 0.250 mL sample was filtered using a 30,000 NMWL filter (Millipore UltraFree-MC) centrifuged for 2 minute at 12,000 RPM. A portion of the filtered reaction sample was diluted 1:20 with dd water and analyzed for peracid using the HPLC assay method (Table 3).

TABLE 3

Lipase-catalyzed Perhydrolysis of 250 mM or 500 mM Triacetin at pH 4.0.

| enzyme | triacetin (mM) | $H_2O_2$ (mM) | peracetic acid (ppm), 5 min | peracetic acid (ppm), 30 min |
|---|---|---|---|---|
| no enzyme | 250 | 500 | 10 | 10 |
| ICR-101 | 250 | 500 | 461 | 1030 |
| ICR-110 | 250 | 500 | 498 | 568 |
| no enzyme | 250 | 2500 | 17 | 15 |
| ICR-101 | 250 | 2500 | 656 | 1158 |
| ICR-110 | 250 | 2500 | 1570 | 2880 |
| no enzyme | 500 | 2500 | 10 | 207 |
| ICR-101 | 500 | 2500 | 612 | 1109 |
| ICR-110 | 500 | 2500 | 1860 | 3755 |

EXAMPLE 4

Lipase-catalyzed Perhydrolysis of a Mixture of Diacetin, Triacetin and Monoacetin at pH 6.5

Into a 4-mL glass vial with stir bar was added 1 mg enzyme (ICR 101-117, BioCatalytics, Pasadena, Calif.) in 0.050 mL of 50 mM potassium phosphate buffer (pH 6.5), 0.900 mL of an aqueous mixture containing diacetin (278 mM), triacetin (144 mM) and monoacetin (131 mM) in 50 mM potassium phosphate buffer (pH 6.5), and either 0.052 mL 30% hydrogen peroxide (500 mM final concentration) or 0.026 mL 30% hydrogen peroxide (250 mM final concentration). After stirring for 5 or 30 minutes at 22° C., a 0.250 mL sample was filtered using a 30,000 NMWL filter (Millipore UltraFree-MC) centrifuged for 2 minute at 12,000 RPM. A portion of the filtered reaction samples was diluted 1:10 with dd water and analyzed for hydrogen peroxide, and the remaining portion of the sample was directly analyzed for peracid using the HPLC assay method (Table 4).

TABLE 4

Lipase-catalyzed Perhydrolysis of a Mixture of Diacetin (278 mM), Triacetin (144 mM) and Monoacetin (131 mM) at pH 6.5.

| enzyme | 250 mM $H_2O_2$ peracetic acid (ppm), 5 min | 250 mM $H_2O_2$ peracetic acid (ppm), 30 min | 500 mM $H_2O_2$ peracetic acid (ppm), 5 min | 500 mM $H_2O_2$ peracetic acid (ppm), 30 min |
|---|---|---|---|---|
| no enzyme | 16 | 56 | 19 | 44 |
| ICR-101 | 136 | 250 | 194 | 277 |
| ICR-102 | 127 | 159 | 26 | 232 |
| ICR-103 | 139 | 133 | 275 | 223 |
| ICR-104 | 151 | 174 | 284 | 286 |
| ICR-105 | 0 | 0 | 0 | 0 |
| ICR-106 | 0 | 16 | 29 | 47 |
| ICR-107 | 0 | 102 | 17 | 54 |
| ICR-108 | 3 | 27 | 0 | 7 |
| ICR-109 | 0 | 38 | 38 | 0 |
| ICR-110 | 451 | 384 | 669 | 484 |
| ICR-111 | 0 | 21 | 12 | 43 |
| ICR-112 | 0 | 24 | 20 | 38 |
| ICR-113 | 34 | 202 | 80 | 236 |
| ICR-114 | 0 | 0 | 0 | 0 |
| ICR-115 | 0 | 8 | 11 | 8 |
| ICR-116 | 0 | 7 | 0 | 0 |
| ICR-117 | 114 | 353 | 61 | 456 |

EXAMPLE 5

Lipase-catalyzed Perhydrolysis of a Mixture of Diacetin, Triacetin and Monoacetin at pH 4.0

Into a 4-mL glass vial with stir bar was added 1 mg enzyme (ICR 101, 110, 113, or 117, BioCatalytics, Pasadena, Calif.) in 0.050 mL of 50 mM sodium acetate/acetic acid buffer (pH 4.0), 0.900 mL of an aqueous mixture containing either a) diacetin (278 mM), triacetin (144 mM) and monoacetin (131 mM) in 50 mM sodium acetate/acetic acid buffer (pH 4.0) or b) diacetin (131 mM), triacetin (68 mM) and monoacetin (62 mM) in 50 mM sodium acetate/acetic acid buffer (pH 4.0), and 0.052 mL 30% hydrogen peroxide (500 mM final concentration). After stirring for 5 or 30 minutes at 22° C., a 0.250 mL sample was filtered using a 30,000 NMWL filter (Millipore UltraFree-MC) centrifuged for 2 minute at 12,000 RPM. A portion of the filtered reaction samples was diluted 1:10 with dd water and analyzed for hydrogen peroxide, and the remaining portion of the sample was directly analyzed for peracid using the HPLC assay method (Table 5).

TABLE 5

Lipase-catalyzed Perhydrolysis of Mixtures of Diacetin, Triacetin and Monoacetin at pH 4.0.

| | substrate concentration | | | |
|---|---|---|---|---|
| enzyme | diacetin (131 mM), triacetin (68 mM), monoacetin (62 mM) peracetic acid (ppm), 5 min | peracetic acid (ppm), 30 min | diacetin (278 mM), triacetin (144 mM) monoacetin (131 mM) peracetic acid (ppm), 5 min | peracetic acid (ppm), 30 min |
| no enzyme | 4 | 2 | 1 | 2 |
| ICR-101 | | | 183 | 457 |

TABLE 5-continued

Lipase-catalyzed Perhydrolysis of Mixtures of Diacetin, Triacetin and Monoacetin at pH 4.0.

| | substrate concentration | | | |
|---|---|---|---|---|
| enzyme | diacetin (131 mM), triacetin (68 mM), monoacetin (62 mM) peracetic acid (ppm), 5 min | peracetic acid (ppm), 30 min | diacetin (278 mM), triacetin (144 mM) monoacetin (131 mM) peracetic acid (ppm), 5 min | peracetic acid (ppm), 30 min |
| ICR-110 | 502 | 616 | 982 | 948 |
| ICR-113 | | | 102 | 358 |
| ICR-117 | | | 280 | 896 |

EXAMPLE 6

Protease-catalyzed Perhydrolysis of Acetamide and Diacetamide at pH 4.0

Into a 4-mL glass vial with stir bar was added 1 mg protease (Table 6) in 0.050 mL of 50 mM sodium acetate/acetic acid buffer (pH 4.0), 0.900 mL of an aqueous mixture containing either a) acetamide (278 mM) in 50 mM sodium acetate/acetic acid buffer (pH 4.0) or b) diacetamide (278 mM) in 50 mM sodium acetate/acetic acid buffer (pH 4.0), and 0.052 mL 30% hydrogen peroxide (500 mM final concentration). After stirring for 5 or 30 minutes at 22° C., a 0.250 mL sample was filtered using a 30,000 NMWL filter (Millipore UltraFree-MC) centrifuged for 2 minute at 12,000 RPM. A portion of the filtered reaction samples was diluted 1:10 with dd water and analyzed for hydrogen peroxide, and the remaining portion of the sample was directly analyzed for peracid using the HPLC assay method (Table 7).

TABLE 6

Protease and Supplier.

| enzyme, source | catalog number | supplier |
|---|---|---|
| Protease Type XIII, *Aspergillus saitoi* | P2143 | Sigma |
| Protease Type XVIII, *Rhizopus* sp. | P5027 | Sigma |
| Protease, *Bacillus* sp. | P5985 | Sigma |
| Pepsin, porcine stomach | P6887 | Sigma |
| Chymopapain, papaya latex | C8526 | Sigma |
| Bromelain, pineapple stem | 3000 GDU | Hong Mao Biochemicals |
| Papain, papaya latex | P3125 | Sigma |
| Pronase, *S. griseus* | 81748 | Biochemika |
| Proteinase K, *T. album*, recombinantly expressed in *P. pastoris* | 3115879 | Roche |
| Proteinase K, *T. album* | 70663 | Novagen |

TABLE 7

Protease-catalyzed Perhydrolysis of Acetamide (250 mM) and Diacetamide (250 mM) at pH 4.0.

| protease | acetamide (250 mM) peracetic acid (ppm), 5 min | acetamide (250 mM) peracetic acid (ppm), 30 min | diacetamide (250 mM) peracetic acid (ppm), 5 min | diacetamide (250 mM) peracetic acid (ppm), 30 min |
|---|---|---|---|---|
| no enzyme (control) | 0 | 0 | 4 | 16 |
| Protease Type XIII | 35 | 49 | 88 | 116 |
| Protease Type XVIII | 27 | 41 | 94 | 107 |
| Protease, *Bacillus* sp. | 48 | 61 | 95 | 138 |
| Pepsin | 45 | 65 | 97 | 120 |
| Chymopapain | 66 | 65 | 100 | 131 |
| Bromelain | 57 | 63 | 92 | 130 |
| Papain | 81 | 105 | 135 | 172 |
| Pronase | 2 | 43 | | |
| Proteinase K, *T. album*, recombinantly expressed in *P. pastoris* | 26 | 43 | | |
| Proteinase K, *T. album* | 34 | 49 | | |

EXAMPLE 7

Protease-catalyzed Perhydrolysis of Triacetin at pH 4.0

Into a 4-mL glass vial with stir bar was added 1 mg protease (Table 6) in 0.050 mL of 50 mM sodium acetate/acetic acid buffer (pH 4.0), 0.900 mL of an aqueous mixture containing triacetin (278 mM) in 50 mM sodium acetate/acetic acid buffer (pH 4.0), and 0.052 mL 30% hydrogen peroxide (500 mM final concentration). After stirring for 5 or 30 minutes at 22° C., a 0.250 mL sample was filtered using a 30,000 NMWL filter (Millipore UltraFree-MC) centrifuged for 2 minute at 12,000 RPM. A portion of the filtered reaction samples was diluted 1:10 with dd water and analyzed for hydrogen peroxide, and the remaining portion of the sample was directly analyzed for peracid using the HPLC assay method (Table 8).

TABLE 8

Protease-catalyzed Perhydrolysis of Triacetin (250 mM) at pH 4.0.

| protease | triacetin (250 mM) peracetic acid (ppm), 5 min | triacetin (250 mM) peracetic acid (ppm), 30 min |
|---|---|---|
| no enzyme (control) | 10 | 10 |
| Protease Type XIII | 209 | 358 |
| Protease Type XVIII | 65 | 30 |
| Protease, *Bacillus* sp. | 74 | 55 |
| Pepsin | 65 | 44 |
| Chymopapain | 72 | 57 |
| Bromelain | 83 | 59 |
| Papain | 85 | 48 |

EXAMPLE 8

Protease-catalyzed Perhydrolysis of Triacetin at pH 6.5

Into a 4-mL glass vial with stir bar was added 1 mg protease (Table 6) in 0.050 mL of 50 mM sodium phosphate buffer (pH 6.5), 0.900 mL of an aqueous mixture containing triacetin (278 mM) in 50 mM phosphate buffer (pH 6.5), and 0.052 mL 30% hydrogen peroxide (500 mM final concentration). After stirring for 5 or 30 minutes at 22° C., a 0.250 mL sample was filtered using a 30,000 NMWL filter (Millipore UltraFree-MC) centrifuged for 2 minute at 12,000 RPM. A portion of the filtered reaction samples was diluted 1:10 with dd water and analyzed for hydrogen peroxide, and the remaining portion of the sample was directly analyzed for peracid using the HPLC assay method (Table 9).

TABLE 9

Protease-catalyzed Perhydrolysis of Triacetin (250 mM) at pH 6.5.

| protease | triacetin (250 mM) peracetic acid (ppm), 5 min | triacetin (250 mM) peracetic acid (ppm), 30 min |
|---|---|---|
| no enzyme (control) | 51 | 26 |
| Protease Type XIII | 135 | 136 |
| Protease Type XVIII | 89 | 119 |
| Protease, *Bacillus* sp. | 93 | 64 |
| Pepsin | 111 | 163 |
| Chymopapain | 69 | 167 |
| Bromelain | 161 | 170 |
| Papain | 203 | 142 |

EXAMPLE 9

Protease-catalyzed Perhydrolysis of Acetamide and Diacetamide at pH 6.5

Into a 4-mL glass vial with stir bar was added 1 mg protease (Table 6) in 0.050 mL of 50 mM potassium phosphate buffer (pH 6.5), 0.900 mL of an aqueous mixture containing either a) acetamide (278 mM) in 50 mM potassium phosphate buffer (pH 6.5) or b) diacetamide (278 mM) in 50 mM potassium phosphate buffer (pH 6.5), and 0.052 mL 30% hydrogen peroxide (500 mM final concentration). After stirring for 5 or 30 minutes at 22° C., a 0.250 mL sample was filtered using a 30,000 NMWL filter (Millipore UltraFree-MC) centrifuged for 2 minute at 12,000 RPM. A portion of the filtered reaction samples was diluted 1:10 with dd water and analyzed for hydrogen peroxide, and the remaining portion of the sample was directly analyzed for peracid using the HPLC assay method (Table 10).

TABLE 10

Protease-catalyzed Perhydrolysis of Acetamide (250 mM) and Diacetamide (250 mM) at pH 6.5.

| protease | acetamide (250 mM) peracetic acid (ppm), 5 min | acetamide (250 mM) peracetic acid (ppm), 30 min | diacetamide (250 mM) peracetic acid (ppm), 5 min | diacetamide (250 mM) peracetic acid (ppm), 30 min |
|---|---|---|---|---|
| no enzyme (control) | 23 | 26 | 59 | 62 |
| Pronase | 126 | 168 | 17 | 17 |
| Proteinase K, *T. album*, recombinantly expressed in *P. pastoris* | 150 | 194 | 66 | 99 |
| Proteinase K, *T. album* | 270 | 214 | 104 | 100 |
| no enzyme (control) | 21 | 0 | 0 | 33 |
| Protease Type XIII | 42 | 32 | 218 | 206 |
| Protease Type XVIII | 58 | 33 | 226 | 180 |
| Protease, *Bacillus* sp. | 89 | 73 | 807 | 181 |
| Pepsin | 81 | 67 | 259 | 198 |
| Chymopapain | 94 | 12 | 218 | 170 |
| Bromelain | 108 | 112 | 311 | 202 |
| Papain | 199 | 157 | 342 | 187 |

EXAMPLE 10

Enzymatic Perhydrolysis of Triacetin using a Combination of Lipase and Proteases at pH 4.0 and 6.5

Reaction mixtures were prepared containing 1 mg lipase (ICR 101, ICR-110, or ICR-117, BioCatalytics, Pasadena, Calif.), 0.3 mg Proteinase K (*T. album*), and 1.2 mg of Pronase in 1.0 mL of 50 mM buffer (either sodium acetate/acetic acid buffer at pH 4.0, or potassium phosphate buffer at pH 6.5), additionally containing triacetin (250 mM) and hydrogen peroxide (500 mM). After stirring for 5 or 30 minutes at 22° C., a 0.250 mL sample was filtered using a 30,000 NMWL filter (Millipore UltraFree-MC) centrifuged for 2 minute at 12,000 RPM. A portion of the filtered reaction samples was diluted 1:10 with dd water and analyzed for hydrogen peroxide, and the remaining portion of the sample was directly analyzed for peracid using the HPLC assay method (Table 11). Reactions were also run with lipase alone or protease(s) alone for comparison of peracetic acid concentrations produced without the combination of lipase and protease(s).

TABLE 11

Enzymatic Perhydrolysis of Triacetin (250 mM) using a Combination of Lipase and Proteases at pH 4.0 and 6.5.

| enzyme source | pH | peracetic acid (ppm), 5 min | peracetic acid (ppm), 30 min |
|---|---|---|---|
| no enzyme (control) | 4.0 | 10 | 10 |
| Proteinase K | 4.0 | 24 | 7 |
| Pronase | 4.0 | 17 | 5 |
| Proteinase K/Pronase | 4.0 | 8 | 15 |
| ICR-101 | 4.0 | 238 | 555 |
| Proteinase K/Pronase/ICR101 | 4.0 | 252 | 542 |
| ICR-110 | 4.0 | 362 | 688 |
| Proteinase K/Pronase/ICR110 | 4.0 | 460 | 679 |
| ICR-117 | 4.0 | 284 | 927 |
| Proteinase K/Pronase/ICR117 | 4.0 | 401 | 909 |
| no enzyme (control) | 6.5 | 22 | 59 |
| Proteinase K | 6.5 | 323 | 669 |
| Pronase | 6.5 | 114 | 484 |
| Proteinase K/Pronase | 6.5 | 225 | 433 |
| ICR-101 | 6.5 | 306 | 588 |
| Proteinase K/Pronase/ICR101 | 6.5 | 359 | 576 |
| ICR-110 | 6.5 | 337 | 398 |
| Proteinase K/Pronase/ICR110 | 6.5 | 406 | 364 |
| ICR-117 | 6.5 | 438 | 984 |
| Proteinase K/Pronase/ICR117 | 6.5 | 579 | 1189 |

EXAMPLE 11 COMPARATIVE

Enzymatic Perhydrolysis of Propyl Acetate or Triacetin at pH 6.5

Into a 4-mL glass vial with stir bar was added 2 mg of one of the following enzymes: acetylcholinesterase (Sigma, C-2888), Lipase G "Amano" 50 (Amano), or Chirazyme L2, lyo. (*C. antartica* lipase B, BioCatalytics) dissolved in 0.050 mL of 50 mM potassium phosphate buffer (pH 6.5). To the vial was then added either a) 0.930 mL of a solution containing 50 mM potassium phosphate buffer (pH 6.5) and 215 mM propyl acetate, followed by 0.021 mL 30% hydrogen peroxide (200 mM final hydrogen peroxide concentration) or b) 0.900 mL of a solution containing 278 mM triacetin in 50 mM potassium phosphate buffer (pH 6.5), 0.024 mL of 50 mM potassium phosphate buffer (pH 6.5), and 0.026 mL 30% hydrogen peroxide (250 mM final concentration). After stirring for 5 or 30 minutes at 22° C., a 0.250 mL sample of the reaction mixture was filtered using a 30,000 NMWL filter (Millipore UltraFree-MC) centrifuged for 2 minute at 12,000 RPM. A portion of the resulting filtrate was diluted 1:10 with dd water and analyzed for hydrogen peroxide, and the remaining portion of the filtrate was directly analyzed for peracid using the HPLC assay method (Table 12).

TABLE 12

Enzymatic Perhydrolysis of Propyl Acetate (200 mM) or Triacetin (250 mM) at pH 6.5.

| enzyme | propyl acetate (200 mM), $H_2O_2$ (200 mM) peracetic acid (ppm), 5 min | propyl acetate (200 mM), $H_2O_2$ (200 mM) peracetic acid (ppm), 30 min | triacetin (250 mM), $H_2O_2$ (250 mM) peracetic acid (ppm), 5 min | triacetin (250 mM) $H_2O_2$ (250 mM) peracetic acid (ppm), 30 min |
|---|---|---|---|---|
| no enzyme (control) | 12 | 69 | 22 | 70 |
| acetyl cholinesterase | 0 | 0 | | |
| Lipase G "Amano" 50 | 18 | 46 | 78 | |
| Chirazyme L2 | 19 | 1 | 192 | 173 |

EXAMPLE 12

Lipase-catalyzed Perhydrolysis of a Mixture of Diacetin, Triacetin and Monoacetin at pH 6.5

A 1-mL reaction mixture was prepared containing 2 mg, 1 mg or 0.2 mg of enzyme (A"Amano"12 lipase (*A. niger* lipase, Amano), Validase lipase AN (*A. niger* lipase, Valley Research), ICR 110 (*C. antartica* lipase, BioCatalytics), Dietrenz CR (*C. rugosa* lipase, Valley Research), Amano F-DS (*R. oryzae* lipase, Amano), Amano DS (*A. niger* lipase, Amano), or Enzeco MLC (Microbial Lipase Concentrate, *A. niger* lipase, Enzyme Development Corporation)) dissolved in 1.0 mL of 50 mM potassium phosphate buffer (pH 6.5) containing a mixture of diacetin (236 mM), triacetin (83 mM) and monoacetin (181 mM) and either 2500 mM or 1000 mM hydrogen peroxide. After stirring for 5 or 30 minutes at 25° C., a 0.250 mL sample was filtered using a 30,000 NMWL filter (Millipore UltraFree-MC) for 2 minute at 12,000 RPM. A portion of the filtered reaction sample was diluted 1:25 with dd water and analyzed for peracid using the HPLC assay method (Table 13).

TABLE 13

Lipase-catalyzed Perhydrolysis of Diacetin (236 mM), Triacetin (83 mM) and Monoacetin (181 mM) at pH 6.5.

| enzyme | [enzyme] (mg/mL) | $H_2O_2$ (mM) | peracetic acid (ppm), 5 min | peracetic acid (ppm), 30 min |
|---|---|---|---|---|
| no enzyme | 0 | 2500 | 80 | 60 |
| A"Amano"12 | 2 | 2500 | 460 | 520 |
| Validase AN | 2 | 2500 | 590 | 510 |
| ICR-110 | 2 | 2500 | 2290 | 2350 |
| A"Amano"12 | 1 | 2500 | 420 | 350 |
| Validase AN | 1 | 2500 | 190 | 390 |
| ICR-110 | 1 | 2500 | 2100 | 2240 |
| ICR-110 | 0.2 | 2500 | 610 | 1850 |
| no enzyme | 0 | 1000 | 90 | 110 |
| A"Amano"12 | 2 | 1000 | 310 | 580 |
| Validase AN | 2 | 1000 | 340 | 550 |
| ICR-110 | 2 | 1000 | 1240 | 1030 |
| A"Amano"12 | 1 | 1000 | 240 | 525 |
| Validase AN | 1 | 1000 | 220 | 470 |
| ICR-110 | 1 | 1000 | 335 | 595 |
| Dietrenz CR | 1 | 1000 | 70 | 240 |
| Amano F-DS | 1 | 1000 | 10 | 10 |
| Amano DS | 1 | 1000 | 170 | 430 |
| Enzeco MLC | 1 | 1000 | 155 | 390 |
| ICR-110 | 0.2 | 1000 | 380 | 410 |
| no enzyme | 0 | 500 | 40 | 30 |
| A"Amano"12 | 1 | 500 | 215 | 490 |
| Validase AN | 1 | 500 | 120 | 500 |
| ICR-110 | 1 | 500 | 240 | 490 |
| Dietrenz CR | 1 | 500 | 0 | 210 |
| Amano F-DS | 1 | 500 | 35 | 75 |
| Amano DS | 1 | 500 | 60 | 305 |
| Enzeco MLC | 1 | 500 | 145 | 405 |

EXAMPLE 13

Lipase-catalyzed Perhydrolysis of a Mixture of Diacetin, Triacetin and Monoacetin at pH 4.0

A 1-mL reaction mixture was prepared containing 2 mg, 1 mg or 0.2 mg of enzyme (A"Amano"12 lipase (*A. niger* lipase, Amano), Validase lipase AN (*A. niger* lipase, Valley Research), or ICR 110 (*C. antartica* lipase, BioCatalytics)) dissolved in 1.0 mL of 50 mM sodium acetate/acetic acid buffer (pH 4.0) containing a mixture of diacetin (236 mM), triacetin (83 mM) and monoacetin (181 mM) and either 2500 mM or 1000 mM hydrogen peroxide. After stirring for 5 or 30 minutes at 25° C., a 0.250 mL sample was filtered using a 30,000 NMWL filter (Millipore UltraFree-MC) for 2 minute at 12,000 RPM. A portion of the filtered reaction sample was diluted 1:25 with dd water and analyzed for peracid using the HPLC assay method (Table 14).

TABLE 14

Lipase-catalyzed Perhydrolysis of Diacetin (236 mM), Triacetin (83 mM) and Monoacetin (181 mM) at pH 4.0.

| enzyme | [enzyme] (mg/mL) | $H_2O_2$ (mM) | peracetic acid (ppm), 5 min | peracetic acid (ppm), 30 min |
|---|---|---|---|---|
| no enzyme | 0 | 2500 | 10 | 40 |
| A"Amano"12 | 2 | 2500 | 870 | 605 |
| Validase AN | 2 | 2500 | 510 | 560 |
| ICR-110 | 2 | 2500 | 1670 | 2250 |
| A"Amano"12 | 1 | 2500 | 240 | 700 |
| Validase AN | 1 | 2500 | 270 | 600 |
| ICR-110 | 1 | 2500 | 1740 | 2180 |
| ICR-110 | 0.2 | 2500 | 480 | 1470 |
| no enzyme | 0 | 1000 | 10 | 10 |
| A"Amano"12 | 2 | 1000 | 320 | 600 |
| Validase AN | 2 | 1000 | 270 | 690 |
| ICR-110 | 2 | 1000 | 1080 | 920 |
| ICR-110 | 0.2 | 1000 | 870 | 1060 |

EXAMPLE 14

Lipase-catalyzed Perhydrolysis of a Mixture of Diacetin, Triacetin and Monoacetin at pH 6.5

A 1-mL reaction mixture was prepared containing 2 mg or 1 mg of enzyme (A"Amano"12 lipase (*A. niger* lipase, Amano), Validase lipase AN (*A. niger* lipase, Valley Research), or ICR 110 (*C. antartica* lipase, BioCatalytics)) dissolved in 1.0 mL of 50 mM potassium phosphate buffer (pH 6.5) containing a mixture of diacetin (500 mM), triacetin (176 mM) and monoacetin (383 mM), and either 2500 mM or 1000 mM hydrogen peroxide. After stirring for 5 or 30 minutes at 25° C., a 0.250 mL sample was filtered using a 30,000 NMWL filter (Millipore UltraFree-MC) for 2 minute at 12,000 RPM. A portion of the filtered reaction sample was diluted 1:25 with dd water and analyzed for peracid using the HPLC assay method (Table 15).

TABLE 15

Lipase-catalyzed Perhydrolysis of a Mixture of Diacetin (500 mM), Triacetin (176 mM) and Monoacetin (383 mM) at pH 6.5.

| enzyme | [enzyme] (mg/mL) | $H_2O_2$ (mM) | peracetic acid (ppm), 5 min | peracetic acid (ppm), 30 min |
|---|---|---|---|---|
| no enzyme | 0 | 2500 | 11 | 13 |
| A"Amano"12 | 2 | 2500 | 394 | 860 |
| Validase AN | 2 | 2500 | 354 | 650 |
| ICR-110 | 2 | 2500 | 5224 | 7130 |
| A"Amano"12 | 1 | 2500 | 290 | 710 |
| Validase AN | 1 | 2500 | 220 | 450 |
| ICR-110 | 1 | 2500 | 3290 | 6130 |
| no enzyme | 0 | 1000 | 70 | 50 |
| A"Amano"12 | 2 | 1000 | 420 | 930 |
| Validase AN | 2 | 1000 | 490 | 890 |
| ICR-110 | 2 | 1000 | 2900 | 2600 |

EXAMPLE 15

Lipase-catalyzed Perhydrolysis of a Mixture of Diacetin, Triacetin and Monoacetin at pH 4.0

A 1-mL reaction mixture was prepared containing 2 mg or 1 mg of enzyme (A"Amano"12 lipase (*A. niger* lipase, Amano), Validase lipase AN (*A. niger* lipase, Valley Research), or ICR 110 (*C. antartica* lipase, BioCatalytics)) dissolved in 1.0 mL of 50 mM sodium acetate/acetic acid buffer (pH 4.0) containing a mixture of diacetin (500 mM), triacetin (176 mM) and monoacetin (383 mM), and either 2500 mM or 1000 mM hydrogen peroxide. After stirring for 5 or 30 minutes at 25° C., a 0.250 mL sample was filtered using a 30,000 NMWL filter (Millipore UltraFree-MC) for 2 minute at 12,000 RPM. A portion of the filtered reaction sample was diluted 1:25 with dd water and analyzed for peracid using the HPLC assay method (Table 16).

TABLE 16

Lipase-catalyzed Perhydrolysis of a mixture of Diacetin (500 mM), Triacetin (176 mM) and Monoacetin (383 mM) at pH 4.0.

| enzyme | [enzyme] (mg/mL) | $H_2O_2$ (mM) | peracetic acid (ppm), 5 min | peracetic acid (ppm), 30 min |
|---|---|---|---|---|
| no enzyme | 0 | 2500 | 10 | 10 |
| A"Amano"12 | 2 | 2500 | 380 | 920 |
| Validase AN | 2 | 2500 | 440 | 930 |
| ICR-100 | 2 | 2500 | 5760 | 7210 |
| A"Amano"12 | 1 | 2500 | 180 | 480 |
| Validase AN | 1 | 2500 | 170 | 520 |
| ICR-110 | 1 | 2500 | 3960 | 7450 |
| no enzyme | 0 | 1000 | 10 | 10 |
| A"Amano"12 | 2 | 1000 | 380 | 900 |
| Validase AN | 2 | 1000 | 400 | 1150 |
| ICR-110 | 2 | 1000 | 2970 | 2510 |

EXAMPLE 16

Lipase-catalyzed Perhydrolysis of Triacetin at pH 6.5

A 1-mL reaction mixture was prepared containing 2 mg, 1 mg or 0.2 mg of enzyme (A"Amano"12 lipase (*A. niger* lipase, Amano), Validase lipase AN (*A. niger* lipase, Valley Research), and ICR 110 (*C. antartica* lipase, BioCatalytics)) dissolved in 1.0 mL of 50 mM potassium phosphate buffer (pH 6.5) containing 500 mM triacetin and either 2500 mM or 1000 mM hydrogen peroxide. After stirring for 5 or 30 minutes at 25° C., a 0.250 mL sample was filtered using a 30,000 NMWL filter (Millipore UltraFree-MC) for 2 minute at 12,000 RPM. A portion of the filtered reaction sample was diluted 1:25 with dd water and analyzed for peracid using the HPLC assay method (Table 17).

TABLE 17

Lipase-catalyzed Perhydrolysis of Triacetin (500 mM) at pH 6.5.

| enzyme | [enzyme] (mg/mL) | $H_2O_2$ (mM) | peracetic acid (ppm), 5 min | peracetic acid (ppm), 30 min |
|---|---|---|---|---|
| no enzyme | 0 | 2500 | 80 | 170 |
| A"Amano"12 | 2 | 2500 | 800 | 1390 |
| Validase AN | 2 | 2500 | 790 | 1180 |
| ICR-110 | 2 | 2500 | 2710 | 2880 |
| A"Amano"12 | 1 | 2500 | 670 | 1070 |
| Validase AN | 1 | 2500 | 460 | 810 |
| ICR-110 | 1 | 2500 | 1840 | 2421 |
| ICR-110 | 0.2 | 2500 | 1120 | 760 |
| no enzyme | 0 | 1000 | 130 | 80 |
| A"Amano"12 | 2 | 1000 | 970 | 1250 |
| Validase AN | 2 | 1000 | 770 | 1310 |
| ICR-110 | 2 | 1000 | 760 | 1400 |
| ICR-110 | 0.2 | 1000 | 450 | 680 |

EXAMPLE 17

Lipase-catalyzed Perhydrolysis of Triacetin at pH 4.0

A 1-mL reaction mixture was prepared containing 2 mg, 1 mg or 0.2 mg of enzyme (A"Amano"12 lipase (*A. niger* lipase, Amano), Validase lipase AN (*A. niger* lipase, Valley Research), or ICR 110 (*C. antartica* lipase, BioCatalytics)) dissolved in 1.0 mL of 50 mM sodium acetate/acetic acid buffer (pH 4.0) containing triacetin (500 mM) and either 2500 mM or 1000 mM hydrogen peroxide. After stirring for 5 or 30 minutes at 25° C., a 0.250 mL sample was filtered using a 30,000 NMWL filter (Millipore UltraFree-MC) for 2 minute at 12,000 RPM. A portion of the filtered reaction sample was diluted 1:25 with dd water and analyzed for peracid using the HPLC assay method (Table 18).

TABLE 18

Lipase-catalyzed Perhydrolysis of Triacetin (500 mM) at pH 4.0.

| enzyme | [enzyme] (mg/mL) | $H_2O_2$ (mM) | peracetic acid (ppm), 5 min | peracetic acid (ppm), 30 min |
|---|---|---|---|---|
| no enzyme | 0 | 2500 | 10 | 20 |
| A"Amano"12 | 2 | 2500 | 1030 | 1370 |
| Validase AN | 2 | 2500 | 920 | 840 |
| ICR-110 | 2 | 2500 | 2810 | 3700 |
| A"Amano"12 | 1 | 2500 | 570 | 740 |
| Validase AN | 1 | 2500 | 570 | 680 |
| ICR-110 | 1 | 2500 | 2120 | 2860 |
| ICR-110 | 0.2 | 2500 | 510 | 780 |
| no enzyme | 0 | 1000 | 5 | 5 |
| A"Amano"12 | 2 | 1000 | 1100 | 1520 |
| Validase AN | 2 | 1000 | 930 | 1230 |
| ICR-110 | 2 | 1000 | 1540 | 1670 |
| ICR-110 | 0.2 | 1000 | 370 | 600 |

EXAMPLE 18

CALB L-catalyzed Perhydrolysis of Triacetin at pH 4.0 and pH 6.5

A 1-mL reaction mixture was prepared containing 0.010 mL of CALB L lipase (a commercial liquid formulation of *C. antartica* lipase B, Novozymes) dissolved in either 1.0 mL of 50 mM sodium acetate/acetic acid buffer (pH 4.0) or 1.0 mL of 50 mM potassium phosphate buffer (pH 6.5) additionally containing triacetin (250 mM) and hydrogen peroxide (2500 mM). After stirring for 5 or 30 minutes at 25° C., a 0.250 mL sample was filtered using a 30,000 NMWL filter (Millipore UltraFree-MC) for 2 minute at 12,000 RPM. A portion of the filtered reaction sample was diluted 1:20 with dd water and analyzed for peracid using the HPLC assay method (Table 19).

TABLE 19

Lipase-catalyzed Perhydrolysis of Triacetin (250 mM) at pH 4.0 or pH 6.5 using CALB L.

| enzyme | pH | $H_2O_2$ (mM) | peracetic acid (ppm), 5 min | peracetic acid (ppm), 30 min |
|---|---|---|---|---|
| no enzyme | 4.0 | 2500 | 28 | 15 |
| CALB L | 4.0 | 2500 | 439 | 1120 |
| no enzyme | 6.5 | 2500 | 226 | 108 |
| CALB L | 6.5 | 2500 | 1294 | 678 |

EXAMPLE 19

Perhydrolysis of Triacetin at pH 4.0 using Immobilized *C. antartica* lipase B

A reaction mixture was prepared containing 100 mg of IMB-111 (immobilized *Candida antartica* lipase B, BioCatalytics) suspended in 10.0 mL of 50 mM sodium acetate/acetic acid buffer (pH 4.0) additionally containing triacetin (500 mM) and hydrogen peroxide (2500 mM). After mixing on a rotating platform for a predetermined time from 2 to 30 minutes at 25° C., a 0.100 mL sample of the liquid portion was filtered using a 30,000 NMWL filter (Millipore UltraFree-MC) for 2 minute at 12,000 RPM. A portion of the filtered reaction sample was diluted 1:20 with dd water and analyzed for peracid using the HPLC assay method (Table 20).

TABLE 20

Lipase-catalyzed Perhydrolysis of Triacetin (500 mM) at pH 4.0 using immobilized *Candida Antartica* lipase B (IMB-111).

| Time (min) | no enzyme, peracetic acid (ppm) | 10 mg/mL IMB-111, peracetic acid (ppm) |
|---|---|---|
| 2 | 42 | 911 |
| 5 | 50 | 1667 |
| 10 | 49 | 2244 |
| 15 | 24 | 2755 |
| 20 | 43 | 3261 |
| 25 | 49 | 3369 |
| 30 | 57 | 3757 |

The above reaction was repeated with fresh catalyst, and after 30 min, the concentration of peracetic acid was 3621 ppm. The catalyst was recovered from the reaction mixture, washed twice with 10.0 mL of 50 mM sodium acetate/acetic acid buffer (pH 4.0), and the reaction was repeated using the recovered enzyme; after 30 min, the concentration of peracetic acid was 2274 ppm.

EXAMPLE 20

Timecourse for Enzymatic Perhydrolysis of Triacetin at pH 6.5

A reaction mixture containing 1.0 mg/mL of DS lipase (*A. niger*, Amano) dissolved in 50 mM potassium phosphate buffer (pH 6.5) containing hydrogen peroxide (2500 mM) and triacetin (500 mM) was stirred at 25° C.

A 0.100 mL aliquot was withdrawn at pre-determined times and filtered using a 30,000 NMWL filter (Millipore UltraFree-MC) for 2 minute at 12,000 RPM. A portion of the filtered reaction sample was diluted 1:20 with dd water and analyzed for peracid using the HPLC assay method (Table 21).

TABLE 21

Timecourse for DS Lipase-catalyzed Perhydrolysis of Triacetin (500 mM) at pH 6.5.

| Time (min or h) | no enzyme, peracetic acid (ppm) | 1 mg/mL DS lipase, peracetic acid (ppm) |
|---|---|---|
| 5 min | 10 | 367 |
| 30 min | 149 | 522 |
| 2 h | 26 | 819 |
| 5 h | 78 | 1481 |
| 19 h | 27 | 1895 |

EXAMPLE 21

Biocidal Activity of a Peracetic Acid Formulation Prepared from Triacetin, Hydrogen Peroxide and *C. antartica* lipase B A reaction was performed using Chirazyme L2 lipase (*C. antartica* lipase B) as enzyme catalyst for the production of peracetic acid. Into a 20-mL glass vial equipped with magnetic stir bar was placed 9.00 mL of 278 mM triacetin in 50 mM phosphate buffer (pH 6.5), 0.258 mL of 30% hydrogen peroxide, and 1.0 mL of 20 mg/mL Chirazyme L2 in 50 mM phosphate buffer (pH 6.5), and the resulting mixture stirred for 5 min at room temperature. The reaction was stopped by filtering the product mixture using a 30K NMWL filter unit (Millipore UltraFree-MC) centrifuged for 2 minute at 12,000 rpm to remove the enzyme, and storing the filtrate on wet ice. The filtrate was analyzed for peracetic acid (PAA) and hydrogen peroxide using the HPLC assay method; control reactions were performed in the absence of added enzyme with and without triacetin. The filtered enzyme-generated product mixture contained 192 ppm PAA, produced from both the chemical and enzymatic reaction of triacetin with hydrogen peroxide; the hydrogen peroxide concentration in the product mixture was 6431 ppm. The control reaction performed with 250-mM triacetin and no added enzyme produced 22 ppm PAA generated from the chemical reaction of triacetin and hydrogen peroxide.

TABLE 22

Dilution Series Used to Assessing Biocidal Activity.

| dilution factor | PAA (ppm) | $H_2O_2$ (ppm) |
|---|---|---|
| 1:5 | 38.3 | 1286 |
| 1:10 | 19.2 | 643 |
| 1:20 | 9.6 | 322 |
| 1:40 | 4.8 | 161 |
| 1:80 | 2.4 | 80 |

The 1:5 dilution and four serial dilutions were evaluated for biocidal activity by mixing 0.100 mL of the PAA-containing solution with 0.100 mL of an inoculum containing $2.7 \times 10^6$ CFU/mL of *E. coli* ATCC 11229 (American Type Culture Collection, Manassas, Va.) in Millers LB broth diluted with Butterfield Buffer; eight replicates of each mixture were contained in individual wells of a sterile 96-well microtiter plate. After the resulting cell suspensions were allowed to stand for 10 minutes at room temperature, they were tested for viability using the growth indicator XTT (2,3-bis[2-methoxy-4-nitro-5-sulfophenyl]-5-[(phenylamino)carbonyl]-2H-tetrazolium, inner salt, monosodium salt; CAS RN 111072-31-2) according to the method of Gabrielson et al. (*J. Microbiol. Methods*, 50:63-73 (2002)). No cell growth of $1.35 \times 10^6$ CFU/mL (indicated by no OD measurement at 450 nm using XTT) was observed with a Minimum Biocidal Concentration of PAA of 2.4 ppm (six-log kill) (Table 23).

TABLE 23

Determination of Minimum Biocidal Concentration (MBC) of Peracetic Acid Generated by Lipase-catalyzed Perhydrolysis of Triacetin for *E. coli* ATCC 11229.

|  |  |  |  |  |  | control | blank |
|---|---|---|---|---|---|---|---|
| PAA (ppm) | 19.15 | 9.6 | 4.8 | 2.4 | 1.2 | 0 |  |
| $H_2O_2$ (ppm) | 643.1 | 321.6 | 160.8 | 80.4 | 40.2 | 0 |  |
| replicate 1 OD (450 nm) | 0.403 | 0.427 | 0.418 | 0.406 | 0.692 | 2.177 | 0.418 |
| replicate 2 OD (450 nm) | 0.383 | 0.398 | 0.393 | 0.400 | 0.674 | 2.142 | 0.415 |
| replicate 3 OD (450 nm) | 0.379 | 0.392 | 0.388 | 0.397 | 0.635 | 2.007 | 0.414 |
| replicate 4 OD (450 nm) | 0.387 | 0.395 | 0.399 | 0.403 | 0.658 | 2.114 | 0.418 |
| replicate 5 OD (450 nm) | 0.381 | 0.404 | 0.398 | 0.401 | 0.625 | 2.171 | 0.409 |
| replicate 6 OD (450 nm) | 0.382 | 0.409 | 0.404 | 0.409 | 0.639 | 2.347 | 0.405 |
| replicate 7 OD (450 nm) | 0.382 | 0.394 | 0.401 | 0.407 | 0.520 | 2.323 | 0.407 |
| replicate 8 OD (450 nm) | 0.403 | 0.422 | 0.471 | 0.543 | 0.496 | 2.582 | 0.428 |
| mean replicate OD (450 nm) | 0.388 | 0.405 | 0.409 | 0.421 | 0.617 | 2.233 | 0.414 |
| blank-corrected mean OD: | −0.029 | −0.009 | −0.005 | 0.007 | 0.203 | 1.819 | 0 |

The filtered enzyme-generated product mixture was diluted 1:5 with sterile water, and the resulting solution was further diluted with sterile water in four 1:1 serial dilutions to obtain the concentrations of PAA and hydrogen peroxide listed in Table 22.

Separately, the cell inoculum was treated with sterile solutions of triacetin (Table 24) or hydrogen peroxide in 50 mM phosphate buffer (pH 6.5) (Table 25) at the concentrations present in each of the biocide dilutions in 5 Table 23 to determine the MBC for these components of the biocide solution.

TABLE 24

Determination of Minimum Biocidal Concentration (MBC) of Triacetin for *E. coli* ATCC 11229.

|  |  |  |  |  |  | control | blank |
|---|---|---|---|---|---|---|---|
| triacetin (ppm) | 5455 | 2728 | 1364 | 682 | 341 | 0 |  |
| replicate 1 OD (450 nm) | 2.210 | 2.280 | 2.337 | 2.213 | 2.408 | 2.375 | 0.401 |
| replicate 2 OD (450 nm) | 2.136 | 2.208 | 2.265 | 2.156 | 2.507 | 2.397 | 0.420 |
| replicate 3 OD (450 nm) | 2.091 | 2.222 | 2.198 | 2.218 | 2.189 | 2.386 | 0.402 |
| replicate 4 OD (450 nm) | 2.229 | 2.273 | 2.140 | 2.304 | 2.568 | 2.557 | 0.409 |

TABLE 24-continued

Determination of Minimum Biocidal Concentration (MBC) of Triacetin for *E. coli* ATCC 11229.

|  |  |  |  |  |  | control | blank |
|---|---|---|---|---|---|---|---|
| replicate 5 OD (450 nm) | 2.124 | 2.167 | 2.266 | 2.310 | 2.563 | 2.491 | 0.413 |
| replicate 6 OD (450 nm) | 2.263 | 2.358 | 2.485 | 2.560 | 2.601 | 2.582 | 0.410 |
| replicate 7 OD (450 nm) | 2.407 | 2.454 | 2.632 | 2.601 | 2.58 | 2.603 | 0.410 |
| replicate 8 OD (450 nm) | 2.539 | 2.663 | 2.823 | 2.605 | 3.148 | 2.952 | 0.455 |
| mean replicate OD (450 nm) | 2.250 | 2.328 | 2.393 | 2.371 | 2.571 | 2.543 | 0.415 |
| blank-corrected mean OD: | 1.835 | 1.913 | 1.978 | 1.956 | 2.156 | 2.128 | 0 |

TABLE 25

Determination of Minimum Biocidal Concentration (MBC) of Hydrogen Peroxide for *E. coli* ATCC 11229.

|  |  |  |  |  |  | control | blank |
|---|---|---|---|---|---|---|---|
| $H_2O_2$ (ppm) | 680.5 | 340.2 | 170.1 | 85.1 | 42.5 | 0 |  |
| replicate 1 OD (450 nm) | 0.456 | 0.440 | 0.401 | 1.880 | 2.170 | 2.371 | 0.423 |
| replicate 2 OD (450 nm) | 0.436 | 0.428 | 0.422 | 1.793 | 2.082 | 2.226 | 0.417 |
| replicate 3 OD (450 nm) | 0.446 | 0.424 | 0.470 | 1.834 | 2.034 | 2.158 | 0.415 |
| replicate 4 OD (450 nm) | 0.433 | 0.423 | 0.435 | 1.889 | 2.007 | 2.216 | 0.422 |
| replicate 5 OD (450 nm) | 0.440 | 0.439 | 0.402 | 1.815 | 2.027 | 2.372 | 0.417 |
| replicate 6 OD (450 nm) | 0.426 | 0.425 | 0.424 | 1.795 | 1.971 | 2.581 | 0.419 |
| replicate 7 OD (450 nm) | 0.430 | 0.432 | 0.462 | 1.962 | 2.117 | 2.741 | 0.442 |
| replicate 8 OD (450 nm) | 0.453 | 0.452 | 0.414 | 2.153 | 2.666 | 2.821 | 0.439 |
| mean replicate OD (450 nm) | 0.440 | 0.433 | 0.4295 | 1.890 | 2.134 | 2.436 | 0.424 |
| blank-corrected mean OD: | 0.016 | 0.009 | 0.005 | 1.466 | 1.710 | 2.012 | 0 |

The MBC of PAA for *E. coli* ATCC 11229 was >2.4 ppm, measured in the presence of 80 ppm of hydrogen peroxide (Table 23); the MBC for hydrogen peroxide was >170 ppm (Table 25), confirming that the biocidal activity of the PAA test solution was due to PAA and not $H_2O_2$. Triacetin had no biocidal effect at the highest concentration examined (5455 ppm, Table 24). The MBC for PAA generated enzymatically agrees closely with the MBC determined using a commercial source of peracetic acid (Table 26, MBC>2.3 ppm PAA).

TABLE 26

Determination of Minimum Biocidal Concentration (MBC) of Commercially-Available Peracetic Acid for *E. coli* ATCC 11229.

|  |  |  |  |  |  | control | blank |
|---|---|---|---|---|---|---|---|
| PAA (ppm) | 18.75 | 9.4 | 4.7 | 2.3 | 1.15 | 0 |  |
| replicate 1 OD (450 nm) | 0.306 | 0.301 | 0.310 | 0.303 | 1.734 | 2.098 | 0.305 |
| replicate 2 OD (450 nm) | 0.292 | 0.296 | 0.297 | 0.288 | 1.367 | 1.832 | 0.295 |
| replicate 3 OD (450 nm) | 0.289 | 0.290 | 0.294 | 0.292 | 1.343 | 1.816 | 0.295 |
| replicate 4 OD (450 nm) | 0.288 | 0.294 | 0.295 | 0.291 | 1.377 | 1.874 | 0.292 |
| replicate 5 OD (450 nm) | 0.296 | 0.291 | 0.298 | 0.294 | 1.368 | 1.869 | 0.294 |
| replicate 6 OD (450 nm) | 0.294 | 0.294 | 0.294 | 0.292 | 1.378 | 1.874 | 0.290 |
| replicate 7 OD (450 nm) | 0.296 | 0.299 | 0.293 | 0.303 | 1.324 | 1.817 | 0.227 |
| replicate 8 OD (450 nm) | 0.300 | 0.295 | 0.304 | 0.318 | 1.386 | 1.869 | 0.173 |
| mean replicate OD (450 nm) | 0.295 | 0.295 | 0.298 | 0.298 | 1.410 | 1.881 | 0.271 |
| blank-corrected mean OD: | 0.024 | 0.024 | 0.027 | 0.026 | 1.138 | 1.610 | 0 |

What is claimed is:

1. A process for producing a concentrated aqueous peracid solution comprising;
  a) providing a set of peracid reaction components, said components comprising:
    1) at least one substrate selected from the group consisting of:

i) esters having the structure

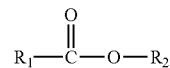

wherein $R_1$=C1 to C10 straight chain or branched chain alkyl optionally substituted with an hydroxyl or a C1 to C4 alkoxy group and $R_2$=C1 to C10 straight chain or branched chain alkyl group, $(CH_2CH_2-O)_nH$ or $(CH_2CH(CH_3)-O)_nH$ and n=1 to 10;

ii) glycerides having the structure

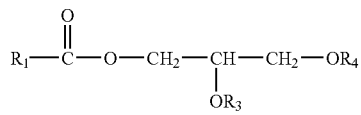

wherein $R_1$=C1 to C10 straight chain or branched chain alkyl optionally substituted with an hydroxyl or a C1 to C4 alkoxy group and $R_3$ and $R_4$ are individually H or $R_1$C(O); and iii) amides having the structure

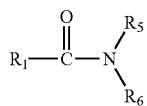

wherein $R_5$ and $R_6$ are individually H, acetyl, or a C1 to C5 straight chain or branched alkyl group;

2) a source of peroxygen that provides a concentration of at least 500 mM hydrogen peroxide upon combining said reaction components; and 3) at least one enzyme catalyst having perhydrolase activity, wherein said enzyme catalyst is selected from the group consisting of lipases, esterases, proteases, and mixtures thereof; and b) combining said reaction components at a pH of about 2.5 to about 7.5, whereby a concentrated peracid solution is produced within at least about 5 minutes to about 2 hours after combining said reaction components.

2. The process of claim 1 wherein the pH is 3 to 7.

3. The process of claim 2 wherein the pH is 4 to 6.5.

4. The process of claim 1 wherein the concentrated peracid solution has a peracid concentration of at least 10 ppm.

5. The process of claim 4 wherein the peracid concentration is at least 100 ppm.

6. The process of claim 5 wherein the peracid concentration is at least 500 ppm.

7. The process of claim 6 wherein the peracid concentration is at least 1000 ppm.

8. The process of claim 7 wherein the peracid concentration is at least 5000 ppm.

9. The process of claim 1 wherein the reaction components comprise at least one lipase and at least one substrate selected from the group consisting of esters, glycerides, and mixtures thereof.

10. The process of claim 1 or claim 9 wherein said at least one substrate is an ester substrate selected from the group consisting of methyl lactate, ethyl lactate, methyl glycolate, ethyl glycolate, methyl methoxyacetate, ethyl methoxyacetate, methyl 3-hydroxybutyrate, ethyl 3-hydroxybutyrate, and mixtures thereof.

11. The process of claim 1 or claim 9 wherein the said at least one substrate is a glyceride substrate selected from the group consisting of monoacetin, diacetin, triacetin, monobutyrin, dibutyrin, tributyrin, glyceryl monooctanoate, glyceryl dioctanoate, glyceryl trioctanoate, and mixtures thereof.

12. The process of claim 11 wherein said glyceride substrate is selected from the group consisting of monoacetin, diacetin, triacetin, and mixtures thereof.

13. The process of claim 1 wherein said at least one enzyme catalyst is at least one lipase produced by an organism selected from the genera *Aspergillus, Rhizopus, Penicillium, Candida, Pseudomonas, Mucor, Thermomyces, Alcaligenes,* and *Sus.*

14. The process of claim 13 wherein said at least one lipase is produced by an organism selected from the group consisting of *Aspergillus* sp., *Aspergillus niger, Rhizopus* sp., *Rhizopus oryzae, Penicillium* sp. I, *Penicillium* sp. II, *Candida* sp., *Candida rugosa, Candida antartia, Pseudomonas* sp., *Pseudomonas cepacia, Pseudomonas fluorescens, Thermomyces lanuginosus, Mucor* sp., and *Mucor miehei*, and *Alcaligenes* sp.

15. The process of claim 14 wherein said at least one lipase is selected from the group consisting of *Aspergillus* sp. lipase, *Aspergillus niger* lipase, *Rhizopus* sp. lipase, *Rhizopus oryzae* lipase, *Penicillium* sp.I lipase, *Penicillium* sp. II lipase, *Candida* sp.lipase, *Candida rugosa* lipase, *Candida antartic* lipase A, *Candida antartica* lipase B, *Pseudomonas* sp. lipase, *Pseudomonas cepacia* lipase, *Pseudomonas fluorescens* lipase, *Thermomyces lanuginosus* lipase, *Mucor* sp. lipase, *Mucor miehei* lipase, *Alcaligenes* sp. lipase, *Sus* sp. lipase, and mixtures thereof.

16. The process of claim 15 wherein said at least one lipase is selected from the group consisting of BioCatalytics ICR-101 *Aspergillus* sp. lipase, BioCatalytics ICR-102 *Rhizopus* sp. lipase, BioCatalytics ICR-103 *Rhizopus oryzae* lipase, BioCatalytics ICR-104 *Penicillium* sp. I lipase, BioCatalytics ICR-105 *Penicillium* sp. II lipase, BioCatalytics ICR-106 *Candida rugosa* lipase, BioCatalytics ICR-107 *Pseudomonas cepacia* lipase, BioCatalytics ICR-108 *Pseudomonas* sp. lipase, BioCatalytics ICR-109 *Pseudomonas fluorescens* lipase, BioCatalytics ICR-110 *Candida antartica* lipase B, BioCatalytics ICR-111 *Candida* sp. lipase, BioCatalytics ICR-112 *Candida antartica* lipase A, BioCatalytics ICR-113 *Pseudomonas* sp. lipase, BioCatalytics ICR-114 porcine pancreas lipase, BioCatalytics ICR-115 *Thermomyces languinosus* lipase, BioCatalytics ICR-116 *Mucor miehei* lipase, BioCatalytics ICR-117 *Alcaligenes* sp. lipase, BioCatalytics IMB-111 immobilized *Candida antartica* lipase B, Amano Lipase AY 30 *Candida rugosa* lipase, Amano Lipase R *Penicillium roqueforti* lipase, Amano Lipase F-AP15 *Rhizopus oryzae* lipase, Amano Lipase M 10 *Mucor javanicus* lipase, Amano Lipase A 12 *Aspergillus niger* lipase, Amano Lipase G 50 *Penicillium camembertii* lipase, Amano F-DS *Rhizopus oryzae* lipase, Amano DS *Aspergillus niger* lipase, Novozym CALB L *Candida antartica* lipase B, Novozym 435 immobilized *Candida antartica* lipase B, and Novozym Palatase 20000L *Aspergillus oryzae* lipase, Lipozyme TL *Thermomyces lanuginosus* lipase, Chirazyme L2 *Candida antartica* lipase B, Validase AN *Aspergillus niger* lipase, Dietrenz CR *Candida rugosa* lipase, Enzeco MLC *Aspergillus niger* lipase, and mixtures thereof.

17. The process of claim 15 wherein said lipase is selected from the group consisting of *Candida antartica* lipase B and *Aspergillus niger* lipase.

18. The process of claim 1 wherein said at least one enzyme catalyst is at least one protease.

19. The process of claim 18 wherein said at least one substrate is selected from the group of esters, glycerides, and mixtures thereof.

20. The process of claim 19 wherein said substrate is an ester substrate selected from the group consisting of methyl lactate, ethyl lactate, methyl glycolate, ethyl glycolate, methyl methoxyacetate, ethyl methoxyacetate, methyl 3-hydroxybutyrate, ethyl 3-hydroxybutyrate, and mixtures thereof.

21. The process of claim 19 wherein said substrate is a glyceride substrate selected from the group consisting of monoacetin, diacetin, triacetin, monobutyrin, dibutyrin, tributyrin, glyceryl monooctanoate, glyceryl dioctanoate, glyceryl trioctanoate, and mixtures thereof.

22. The process of claim 21 wherein the glyceride substrate is selected from the group consisting of monoacetin, diacetin, triacetin, and mixtures thereof.

23. The process of claim 18 wherein said at least one substrate is an amide selected from the group consisting of acetamide, diacetamide, and mixtures of acetamide and diacetamide.

24. The process of claim 18 wherein said at least one protease is produced by an organism selected from the genera *Aspergillus, Rhizopus, Bacillus, Carica, Ananas, Streptomyces, Tritirachium*, and *Sus*.

25. The process of claim 24 wherein said protease is produced from an organism selected from the group consisting of *Aspergillus saitoi, Rhizopus* sp., *Bacillus* sp., *Bacillus subtilis, Sus scrofa, Carica papaya, Ananas comosus, Streptomyces griseus*, and *Tritirachium album*.

26. The process of claim 25 wherein said protease is selected from the group consisting of *Aspergillus saitoi* protease type XIII, *Rhizopus* sp. protease type XVIII, *Bacillus* sp. protease, *Sus scrofa* pepsin, *Carica papaya* Chymopapain, *Carica papaya* papain, *Ananas comosus* bromelain, *Streptomyces griseus* Pronase, *Tritirachium album* Proteinase K, and mixtures thereof.

27. The process of claim 26 wherein said protease is selected from the group consisting of *Streptomyces griseus* Pronase, *Tritirachium album* Proteinase K, and mixtures thereof.

28. The process of claim 18 wherein said at least one protease has prion-degrading activity and perhydrolase activity 29. The process of claim 1 wherein the reaction components comprise at least one lipase and at least one prion-degrading protease.

30. The process of claim 29 wherein the prion-degrading protease is selected from the group consisting of Proteinase K, Pronase, and mixtures thereof.

31. The process of claim 1 wherein the peracid produced is selected from the group consisting of peracetic acid, perbutyric acid, perlactic acid, perglycolic acid, permethoxyacetic acid, per-β-hydroxybutyric acid, peroctanoic acid, and mixtures thereof.

32. The process of claim 31 wherein the peracid is peracetic acid.

* * * * *

UNITED STATES PATENT AND TRADEMARK OFFICE
CERTIFICATE OF CORRECTION

PATENT NO.       : 7,612,030 B2                                      Page 1 of 1
APPLICATION NO.  : 11/413246
DATED            : November 3, 2009
INVENTOR(S)      : DiCosimo et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 404 days.

Signed and Sealed this

Nineteenth Day of October, 2010

David J. Kappos
*Director of the United States Patent and Trademark Office*